(12) United States Patent
Da Silva et al.

(10) Patent No.: US 10,725,056 B2
(45) Date of Patent: Jul. 28, 2020

(54) BIOMARKERS FOR ASSESSING HIV

(71) Applicants: BIOCRATES LIFE SCIENCES AG, Innsbruck (AT); IDCGS CLINICA DE DIAGNOSTICOS MEDICOS, Vila Mariana, Sao Paulo (BR); CENTRO DE GENOMAS, Sao Paulo (BR)

(72) Inventors: Ismael Dale Cotrim Guerreiro Da Silva, Sao Paulo (BR); Edson Guimaraes Loturco, Sao Paulo (BR); Ricoardo Soubie Diaz, Sao Paulo (BR); Therese Koal, Innsbruck (AT)

(73) Assignees: BIOCRATES LIFE SCIENCES AG, Tirol (AT); IDCGS CLINICA DE DIAGNOSTICOS MEDICOS, Sao Paulo (BR); CENTRO DE GENOMAS, Sao Paulo (BR)

( * ) Notice: Subject to any disclaimer, the term of this patent is extended or adjusted under 35 U.S.C. 154(b) by 0 days.

(21) Appl. No.: 15/387,932

(22) Filed: Dec. 22, 2016

(65) Prior Publication Data

US 2017/0160246 A1  Jun. 8, 2017

Related U.S. Application Data

(63) Continuation of application No. 15/301,913, filed as application No. PCT/EP2016/056977 on Mar. 31, 2015, now Pat. No. 10,054,604.

(30) Foreign Application Priority Data

Apr. 4, 2014 (EP) ..................................... 14001259

(51) Int. Cl.
*G01N 33/92* (2006.01)
*G01N 33/68* (2006.01)
(Continued)

(52) U.S. Cl.
CPC ............... *G01N 33/92* (2013.01); *C12Q 1/70* (2013.01); *G01N 33/56988* (2013.01);
(Continued)

(58) Field of Classification Search
None
See application file for complete search history.

(56) References Cited

FOREIGN PATENT DOCUMENTS

| EP | 2 284 540 | | 2/2011 | |
|---|---|---|---|---|
| WO | 94 05814 | | 3/1994 | |
| WO | WO 94/05814 | * | 3/1994 | ............... C12Q 1/70 |

OTHER PUBLICATIONS

Zangerle et al. Increased blood phenylalanine to tyrosine ratio in HIV-1 infection and correction following effective antiretroviral therapy. Brain Behavior Immun. 2010; 24:403-408.*

(Continued)

*Primary Examiner* — Janet L Andres
*Assistant Examiner* — Stuart W Snyder
(74) *Attorney, Agent, or Firm* — Emerson Thomson Bennett, LLC; Daniel A. Thomson

(57) ABSTRACT

The present invention relates to metabolic biomarker sets for assessing HIV. In preferred embodiments, the present invention relates to the use of biomarker sets for screening and/or diagnosing HIV infection, for prediction of immunologic response of a mammalian subject to antiretroviral therapy and/or prognosis of HIV disease progression, and for monitoring of HIV disease activity in a mammalian subject. In other embodiments, the invention relates to methods for screening and/or diagnosing HIV infection, for prediction of immunologic response of a mammalian subject to antiretroviral therapy and/or prognosis of HIV disease progression, and for monitoring of HIV disease activity in a mammalian subject, as well as to a kit adapted to carry out the methods. By employing the specific biomarkers and the method (Continued)

according to the present invention it becomes possible to more properly and reliably assess HIV. In particular, it becomes possible to screen for and diagnose HIV in a patient with high accuracy and predict early in advance the patient's therapeutic response to antiretroviral therapy.

5 Claims, 23 Drawing Sheets

(51) Int. Cl.
  *G01N 33/569* (2006.01)
  *C12Q 1/70* (2006.01)
(52) U.S. Cl.
  CPC ..... *G01N 33/6812* (2013.01); *G01N 33/6893* (2013.01); *G01N 2333/47* (2013.01); *G01N 2405/04* (2013.01); *G01N 2405/08* (2013.01); *G01N 2560/00* (2013.01); *G01N 2800/52* (2013.01)

(56) References Cited

OTHER PUBLICATIONS

Vilaseca et al. Low serum carnitine in HIV-infected children on antiretroviral treatment. Eur. J. Clin. Nut. 2003; 57:1317-1322.*
Kirmse, B., Hobbs, C,V., Peter, I., Laplante, B., Caggana, M. Kloke, K, Raymond, K, Summar, M., Borkowsky, W., "Abnormal Newborn Screening Data and Acylcarnitines in HIV/ARV-Eposed Infants," Pediatr Infect Dis Journal, Feb. 2013, 32(2), 146-150.
Zangerle, R., Widner, B., Quirchmair, G., Neurauter, G., Sarcletti, M., Fuchs, D., "Effective Antiretroviral Therapy Reduces Degradation of Tryptophan in Patients with HIV-1 Infection," Clin Immunol, Sep. 2002, 104(3), 242-7.
Constans, J., Pelichant, E., Pellegrin, J.L. Sergeant, C., Hamon, C., Dubourg, L, Thomas, M.J., Simonoff, M., Pellegrin, I., Brossard G., et al., "Fatty Acids and Plasma Antioxidants in HIV-Positive Patients: Correlation with Nutritional and Immunological Status," Clin Biochem, Aug. 1995, 28(4), 421-6.
Zangerle, R., Kurz, K., Neurauter, G., Kitchen, M., Sarcletti, M., Fuchs, D., "Increased Blood Phenylaianine to Tyrosine Ratio in HIV-1 Infection and Correction Following Effective Antiretroviral Therapy," Brain Behav Immun, Mar. 2010, 24(3), 403-8.
Vilaseca, M.A., Artuch, R., Sierra, C., Pineda, J., Lopez-Vilches, M.A., Munoz-Almagro, C., Fortuny, C., "Low Serum Carnitine in HIV-infected Children on Antiretroviral Treatment," EP Journal of Clinical Nutrition, 2003, 57, 1317-1322.
Wong, G., Trevillyan, J.M., Fatou, B., Cinel, M., Weir, J.M., Hoy, J.F., Meikle, P.J., "Plasma Lipidomic Profiling of Treated HIV-Positive Individuals and the Implications for Cardiovascular Risk Prediction," Apr. 14, 2014, http://dx.doi.org/10.1371/journal.pone.0094810.
Oosthuizen, W.. Van Graan, A., Kruger, A., Vorster, H. H., "Polyunsaturated Fatty Acid Intake is Adversely Related to Liver Function in HIV-Infected Subjects: The THUSA Study13," American Journal of Clinical Nutrition, May 2006, vol. 83, No. 5, 1193-1198.
WIPO, Search Report, WO 2016 150 360, dated Oct. 8, 2015.

* cited by examiner

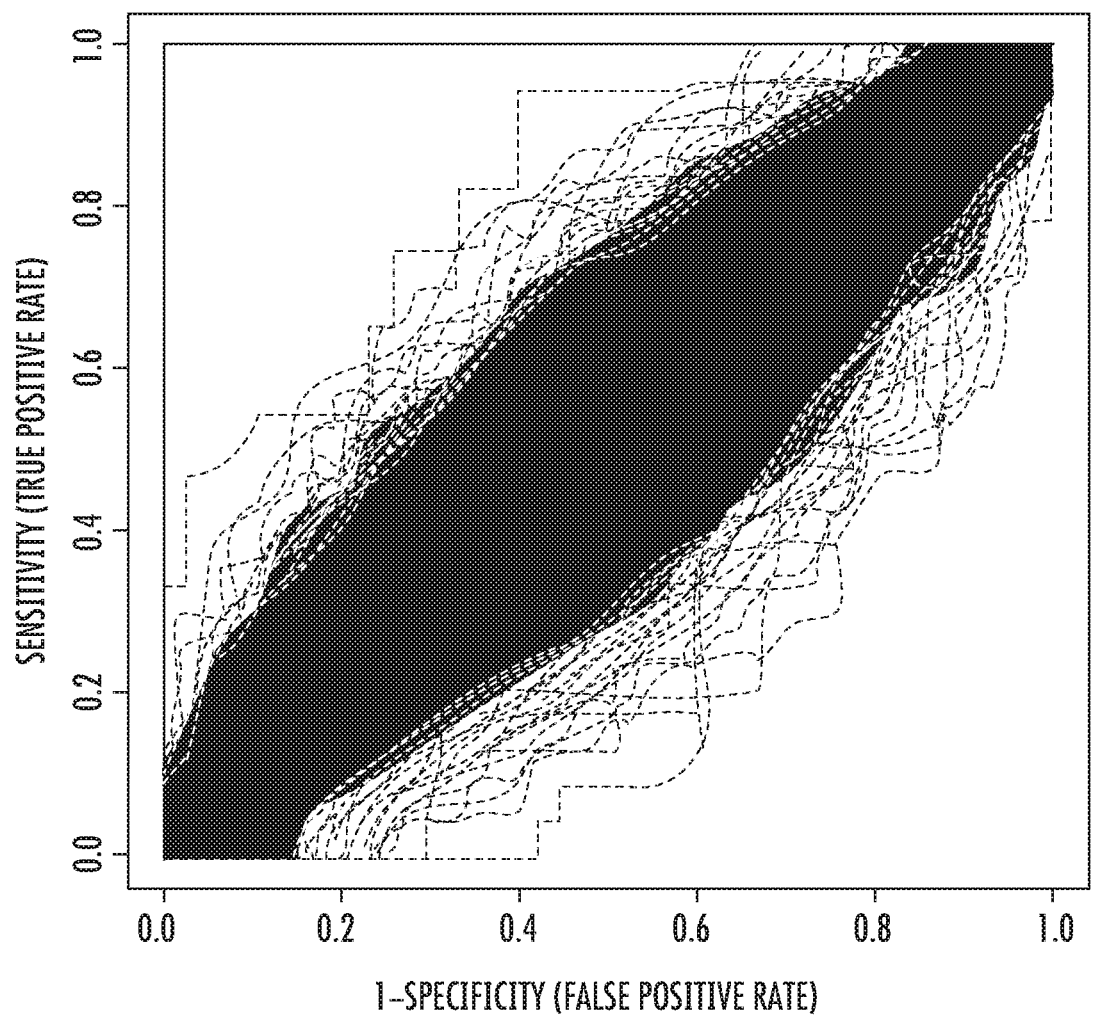
FIG. 3.1

Fig. 3.2
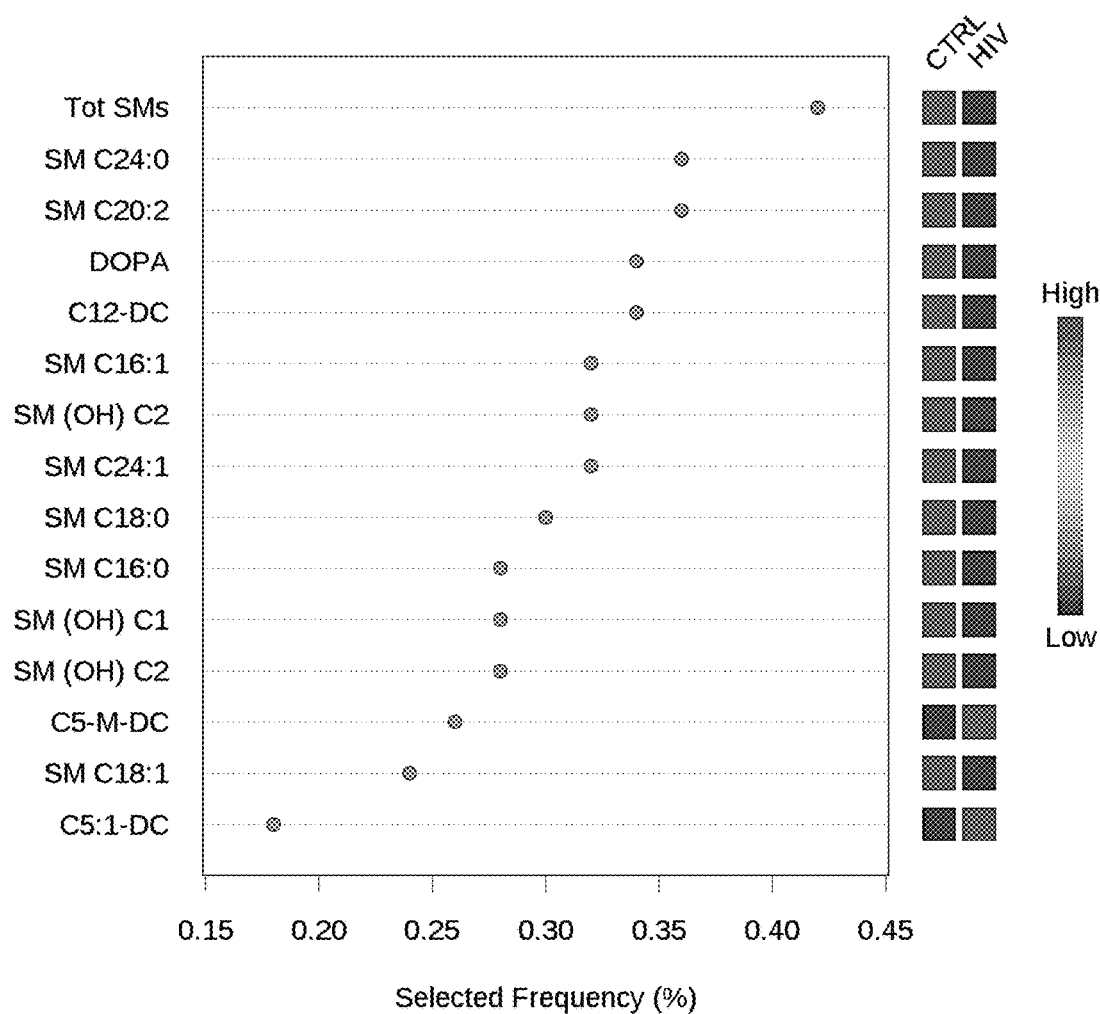

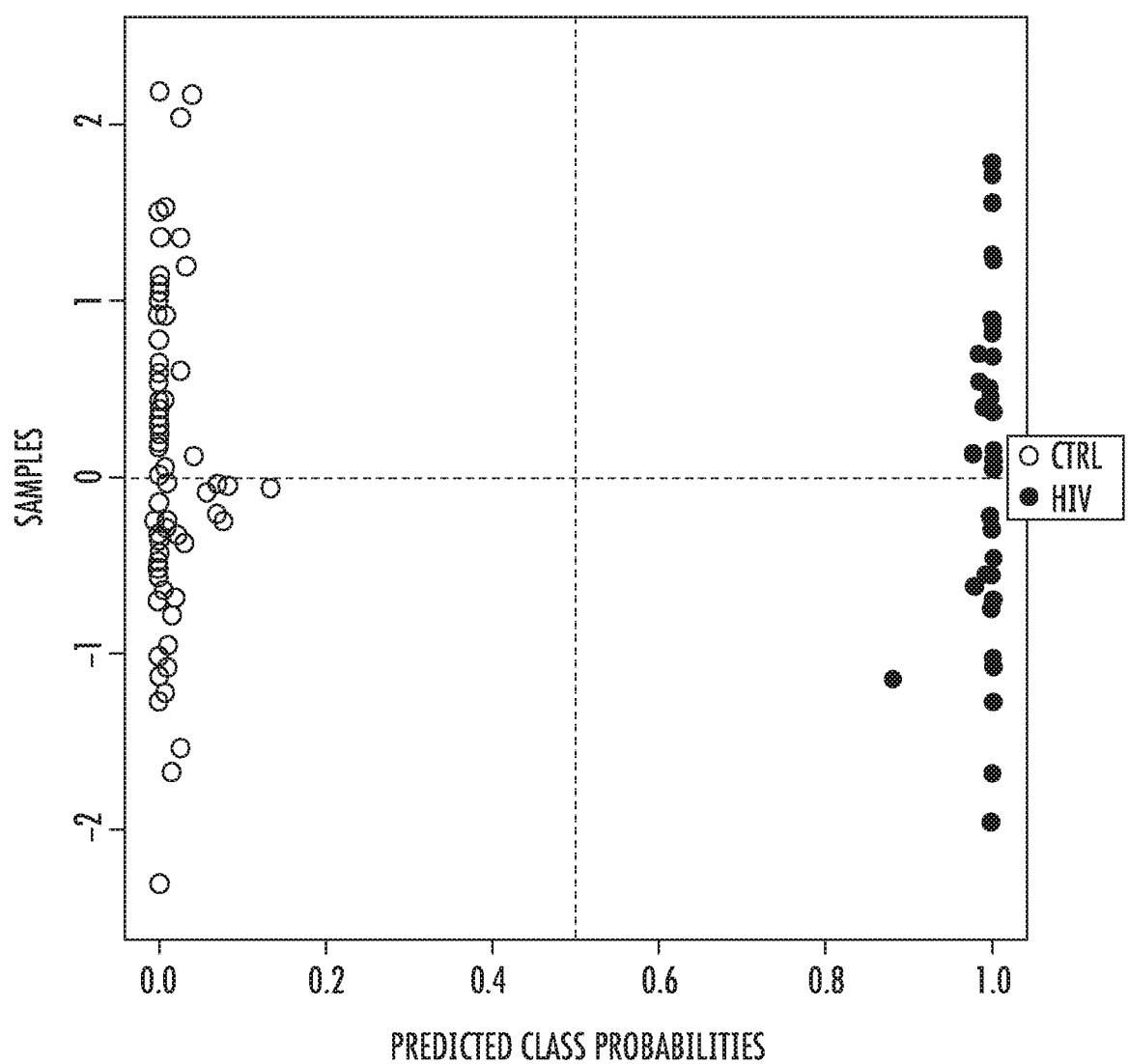
FIG. 4A1

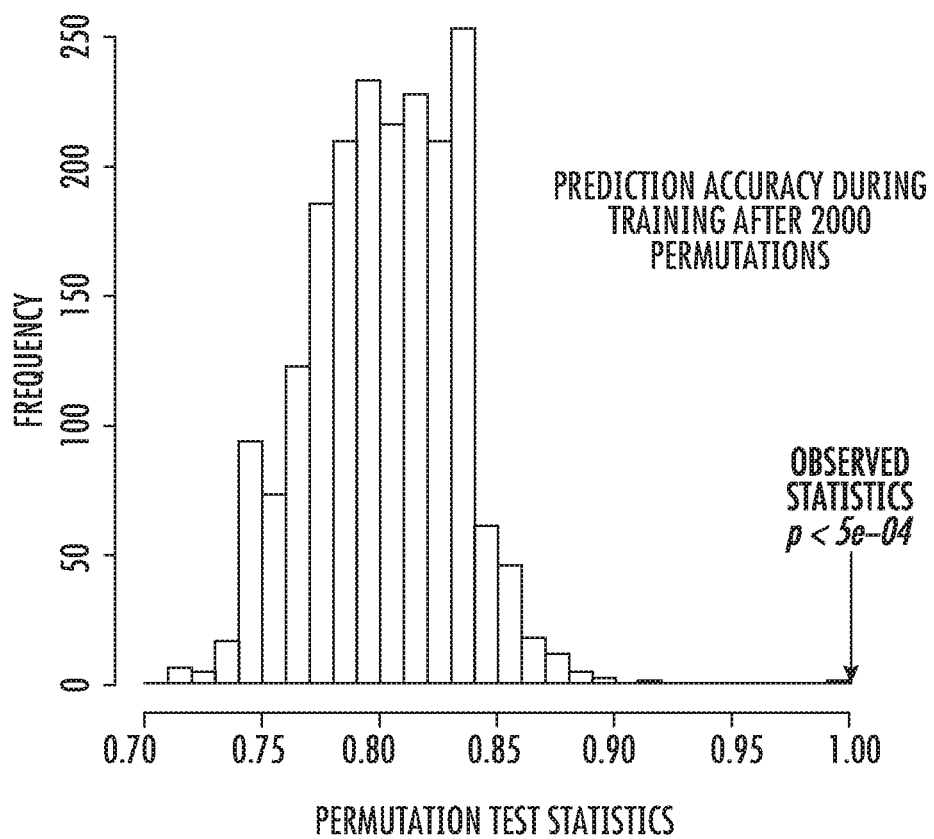
FIG. 4A2

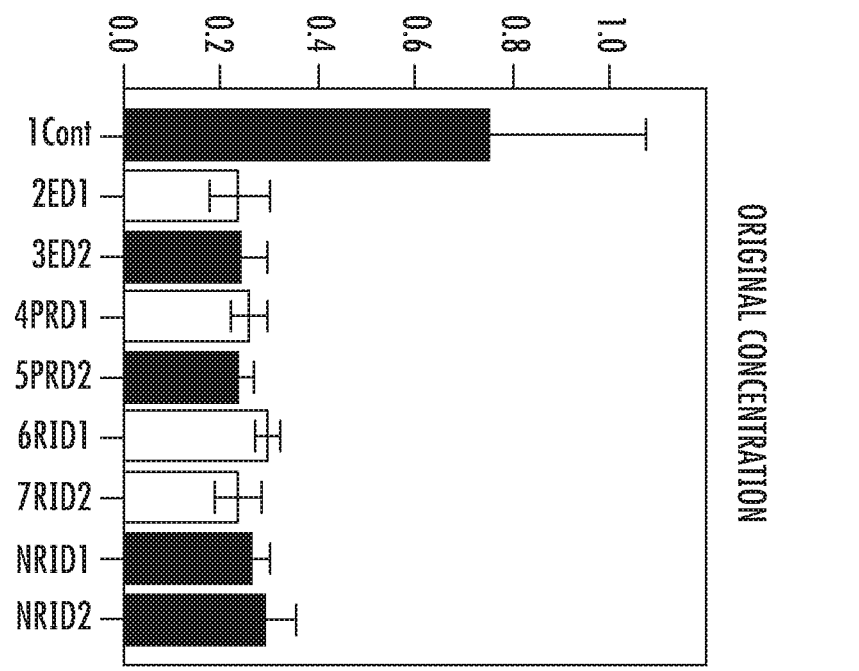
FIG. 5A
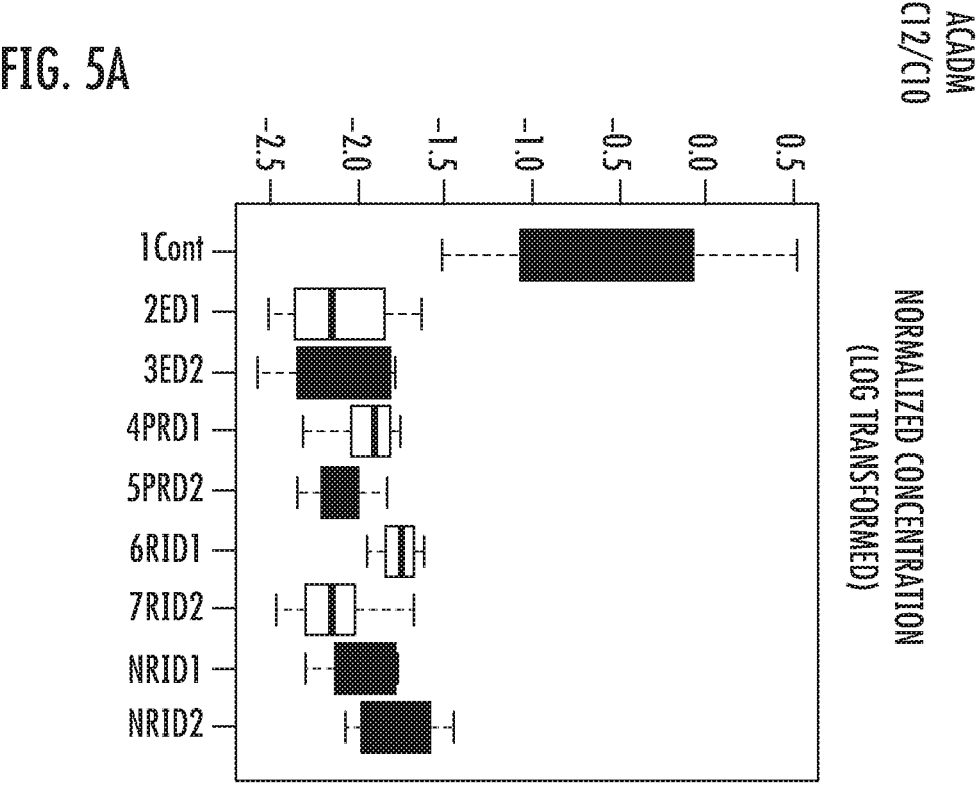

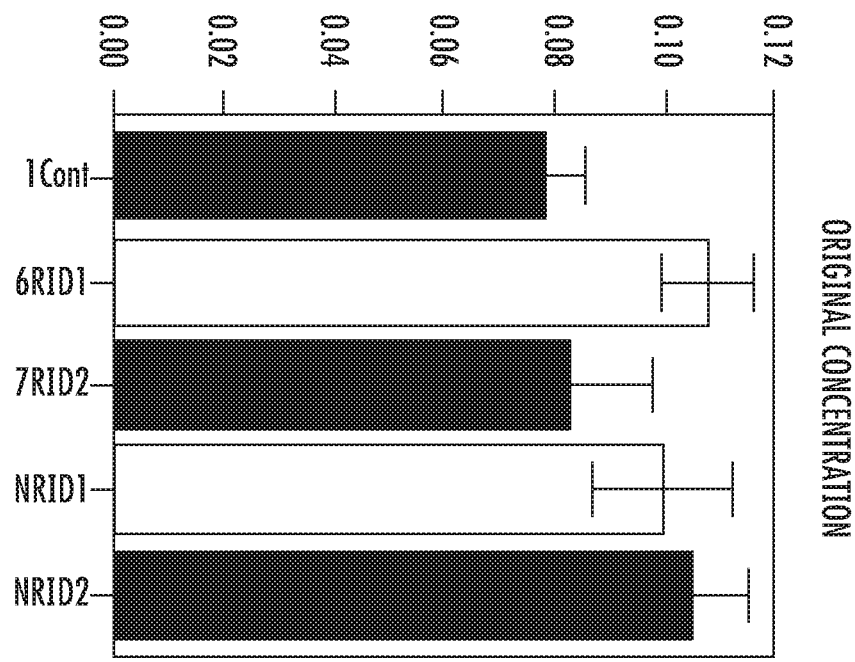
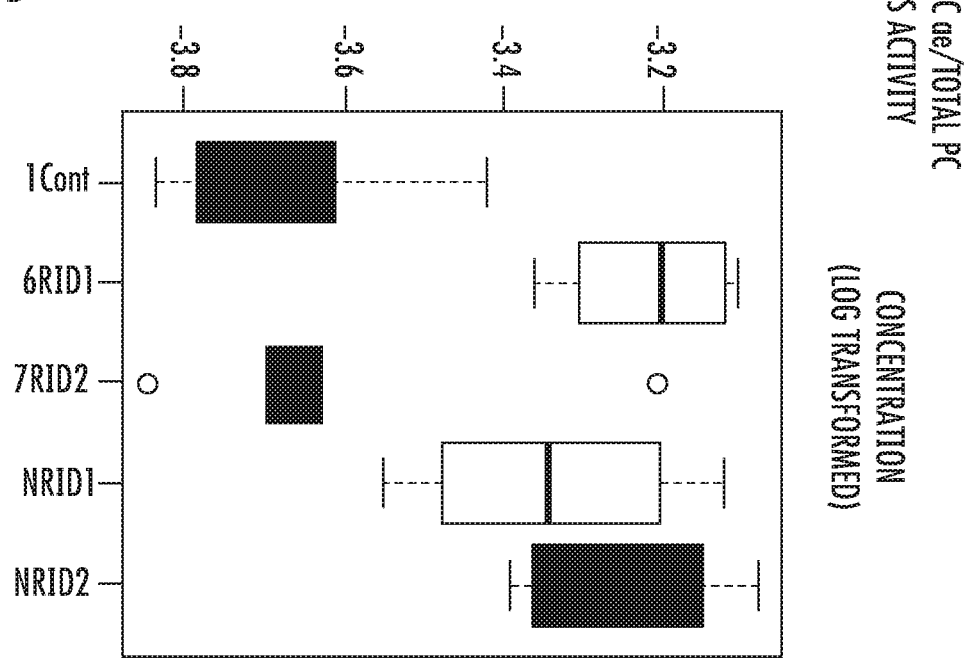
FIG. 7B

BIOMARKERS FOR ASSESSING HIV

TECHNICAL FIELD

The present invention relates to new biomarkers for assessing HIV. In particular, the present invention provides new biomarkers for screening and diagnosing HIV in patients, predicting immunologic response to antiretroviral therapy and prognosis of HIV disease progression, and monitoring HIV disease activity. Moreover, the present invention relates to a method for assessing HIV in a mammalian subject, and to a kit for carrying out the method. More particularly, the present invention is directed to new diagnostic and predictive biomarkers able to identify patients at higher risk to develop incomplete restoration of immune system after antiretroviral treatment as sell as rapid progressors patients.

BACKGROUND ART

Metabolomics

Metabolomics is a comprehensive quantitative measurement of low molecular weight compounds covering systematically the key metabolites, which represent the whole range of pathways of intermediary metabolism The capability to analyze large arrays of metabolites extracts biochemical information reflecting true functional end-points of overt biological events while other functional genomics technologies such as transcriptomics and proteomics, though highly valuable, merely indicate the potential cause for phenotypic response. Therefore they cannot necessarily predict drug effects, toxicological response or disease states at the phenotype level unless functional validation is added.

Metabolomics bridges this information gap by depicting in particular such functional information since metabolite differences in biological fluids and tissues provide the closest link to the various phenotypic responses. Needless to say, such changes in the biochemical phenotype are of direct interest to pharmaceutical, biotech and health industries once appropriate technology allows the cost-efficient mining and integration of this information.

In general, phenotype is not necessarily predicted by genotype. The gap between genotype and phenotype is spanned by many biochemical reactions each with individual dependencies to various influences, including drugs, nutrition and environmental factors. In this chain of biomolecules from the genes to phenotype, metabolites are the quantifiable molecules with the closest link to phenotype. Many phenotypic and genotypic states, such as a toxic response to a drug or disease prevalence are predicted by differences in the concentrations of functionally relevant metabolites within biological fluids and tissue.

HIV/AIDS

Human immunodeficiency virus infection/acquired immunodeficiency syndrome (HIV/AIDS) is a disease of the human immune system caused by infection with human. immunodeficiency virus (HIV). During the initial infection, a person may experience a brief period of influenza-like illness. This is typically followed by a prolonged period without symptoms. As the illness progresses, it interferes more and more with the immune system, making the person much, more likely to get infections, including opportunistic infections and tumors that do not usually affect people who have working immune systems. There is currently no cure or effective HIV vaccine. Treatment consists of antiretroviral therapy (ART), such as high active antiretroviral therapy (HAART) which slows progression of the disease and as of 2010 more than, 6.6 million people were taking them in low and middle income countries.

The United States Center for Disease Control and Prevention created a classification system for HIV, and updated it in 2008. This system classifies HIV infections based on CD4 count and clinical symptoms, and describes the infection in three stages:

Stage 1: CD4 count ≥500 cells/µl and no AIDS defining conditions

Stage 2: CD4 count 200 to 500 cells/µl and no AIDS defining conditions

Stage 3: CD4 count ≤200 cells/µl or AIDS defining conditions

For surveillance purposes, the AIDS diagnosis still stands even if, after treatment, the CD4+ T cell count rises to above 200 per µL of blood or other AIDS-defining illnesses are cured.

However, it is becoming increasingly evident that the CD4 count and viral load do not provide a complete picture of the underlying state of the immune system for HIV patients. Indeed, the extension of life as a consequence of antiretroviral therapies has heralded a new era of non-AIDS-related diseases and incomplete restoration of immune function despite good control of viral loads. Therefore, the identification and incorporation of new predictive markers for HIV diagnosis and classification is of utmost importance.

In sites where antiretroviral drugs have been widely used since the mid-90s, the use of antiretroviral therapy (ART) has changed the natural course of HIV infection, improving the immune system of patients and thus resulting in both reduced incidence of opportunistic infections and increased survival of HIV-infected patients. Recent data shows that in Brazil there has been an increase in survival among patients diagnosed with AIDS, with 63.97% of patients achieving a survival of 108 months. Recently, several efforts have been made in order to understand the pathogenesis of HIV by means of the evaluation of its impact on infected cells, on the discovery of disease biomarkers and the understanding of disease progression through the study of specific subgroups of patients.

Therefore, an urgent need exists in the art for new screening and diagnosing procedures, which can be easily performed and which can provide for more accurate and effective results, as well as for a more reliable prediction of a patient's response to ART.

One promising approach for screening, diagnosing and classifying HIV is the use of biomarkers, such as plasma (or serum) biomarkers (such as antigens and protein patterns). However, they are still far from clinical use.

Pendyala G. and Fox H S. (Proteomic and metabolomic strategies to investigate HIV-associated neurocognitive disorders, Genome Med. 2010; 2(3): 22) describe protein biomarkers for HIV-associated neurocognitive disorders that have been discovered using proteomics, which include complement C3, soluble superoxide dismutase and a prostaglandin synthase. According to the authors, reliable molecular markers could aid in the prediction of development of disease.

Cassol et al. (Plasma metabolomics identifies lipid abnormalities linked to markers of inflammation, microbial translocation, and hepatic function in HIV patients receiving protease inhibitors. BMC Infectious Diseases (2013) 13:203) describe that a 35-metabolite signature mapping to lipid, amino acid, and nucleotide metabolism can distinguish HIV patients with advanced disease on PI-based ART from controls regardless of HCV serostatus. The authors conclude that lipid alterations in HIV patients receiving PI-based ART are linked to markers of inflammation, microbial translocation, and hepatic function, suggesting that therapeutic strategies attenuating dysregulated innate immune activation and hepatic dysfunction may be beneficial for prevention and treatment of metabolic disorders in HIV patients.

Therefore, there is an urgent need in the art to develop new screening and diagnosing techniques suitable for predicting HIV progression, outcome of the disease as well as the patient's therapeutic response to antiretroviral therapy (ART). In particular, new effective biomarkers for HIV screening that can be used individually or in combination with other existing methods are urgently needed.

In view of the above mentioned problems existing in the prior art, the object underlying the present invention is the provision of new biomarkers for assessing HIV, which markers allow for reliable diagnosis of HIV already in an early stage of disease progression. Optimally, the marker should be easily detectable in a biological sample, such as in blood, and its level should be consistently related to the stage of HIV. Moreover, it is an object of the present invention to provide for a method for assessing HIV in a biological sample. Furthermore, the new biomarkers should be suitable for predicting HIV progression, outcome of the disease as well as the patient's therapeutic response to antiretroviral therapy.

In order to solve the objects underlying the present invention the inventors based their investigations on metabolomics as it could give insight in the biochemical changes occurring in the course of HIV development and offer several novel and potentially better biomarkers. The inventors found that a more comprehensive picture of all metabolomics pathways and mechanisms involved in HIV is given when using a panel of metabolites that are altered with progressing HIV rather than employing techniques conventionally performed in the art.

SUMMARY OF THE INVENTION

Therefore, the present invention, as defined in the claims attached, provides for new biomarkers (i.e. a new biomarker set) suitable for assessing HIV infection, particularly at an early stage of disease. Moreover, the present invention also provides for a method for assessing HIV in a mammalian subject, as well as a kit adapted to carry out the method.

In a first embodiment, the invention is directed to the use of a combination of metabolites contained in a blood sample, comprising at least one acylcarnitine (AC) and at least one sphingomyelin (SM) as a biomarker set for screening and/or diagnosing HIV.

In a further embodiment, the invention is directed to the use of a combination of metabolites contained in a blood sample, comprising at least one phosphatidylcholine comprising at least one acyl-alkyl group in the molecule (PC ae), and at least two amino acids as a biomarker set for prediction of immunologic response of a mammalian subject to antiretroviral therapy and/or prognosis of HIV disease progression.

In a further embodiment, the invention is directed to the use of a combination of metabolites contained in a blood sample, comprising at least the ratio of total amount of arachidonic polyunsaturated etherlipids to total amount of monounsaturated fatty acid ether lipids and the ratio of total amount of monounsaturated fatty acid ether lipids to total amount of saturated fatty acids as a biomarker set for monitoring of HIV activity in a mammalian subject.

In a further embodiment, the present invention provides a method for screening and/or diagnosing HIV in a mammalian subject, the method comprising measuring in a blood sample obtained from the subject the amount of at least one acylcarnitine (AC) and at least one sphingomyelin (SM).

In a further embodiment, the present invention provides a method for prediction of immunologic response of a mammalian subject to antiretroviral therapy and/or prognosis of disease progression, the method comprising measuring in a blood sample obtained from the subject the amount of at least one phosphatidylcholine with at least one acyl-alkyl group in the molecule (PC ae) and at least two amino acids.

In a further embodiment, the present invention provides a method for monitoring of HIV activity in a mammalian subject, the method comprising measuring in a blood sample obtained from the subject at least the ratio of total amount of arachidonic polyunsaturated etherlipids to total amount of monounsaturated fatty acid ether lipids and the ratio of total amount of monounsaturated fatty acid ether lipids to total amount of saturated fatty acids.

In particular, the invention comprises the following embodiments.

[1] Use of a combination of metabolites contained in a blood sample, comprising at least one acylcarnitine (AC) and at least one sphingomyelin (SM) as a biomarker set for screening and/or diagnosing HIV infection.

[2] Use of a combination of metabolites contained in a blood sample, comprising at least one phosphatidylcholine comprising at least one acyl alkyl group in the molecule (PC ae), and at least two amino acids as a biomarker set for prediction of immunologic response of a mammalian subject to antiretroviral therapy and/or prognosis of HIV disease progression.

[3] Use of a combination of metabolites contained in a blood sample, comprising at least the ratio of total amount of arachidonic polyunsaturated etherlipids (PUFA ae) to total amount of monounsaturated fatty acid ether lipids (MUFA ae) and the ratio of total amount of monounsaturated fatty acid ether lipids (MUFA ae) to total amount of saturated fatty acids (SFA) as a biomarker set for monitoring of HIV disease activity in a mammalian subject.

[4] A method for screening and diagnosing HIV infection in a mammalian subject, the method comprising measuring in a blood sample obtained from the subject the amount of at least one acylcarnitine (AC) and at least one sphingomyelin (SM).

[5] The method of [4], wherein the at least one acylcarnitine is selected from those included in Table 2 of the specification and/or the at least one sphingomyelin is selected from those included in Table 4 of the specification, respectively.

[6] The method of [4] or [5], wherein the at least one acylcarnitine is selected from glutaconylcarnitine, methylglutarylcarnitine, octanoylcarnitine, decanoylcarnitine, and dodecanoylcarnitine.

[7] The method of anyone of [4] to [6], further comprising at least one biogenic amine and/or at least one phosphatidylcholine.

[8] The method of anyone of [4] to [7], wherein measuring the amount of at least one sphingomyelin comprises measuring the ratio of amount of hydroxysphingomyelin with acyl residue sum of C24:1 (SM(OH) C24:1) to the amount of sphingomyelin with acyl residue sum of C16:0 (SM C16:0).

[9] A method for prediction of immunologic response of a mammalian subject to antiretroviral therapy and/or prognosis of disease progression, the method comprising measuring in a blood sample obtained from the subject the amount of at least one phosphatidylcholine with at least one acyl-alkyl group in the molecule (PC ae) and at least two amino acids.

[10] The method of [9], wherein the at least one phosphatidylcholine with at least one acyl-alkyl group in the molecule (PC ae) is selected from those included in Table 5 of the specification.

[11] The method of [9] or [10], further comprising measuring the amount of at least one acylcarnitine.

[12] The method of [11], wherein the at least one acylcarnitine is selected from those included in Table 2 of the specification.

[13] A method for monitoring of HIV disease activity in a mammalian subject, the method comprising measuring in a blood sample obtained from the subject at least the ratio of total amount of arachidonic polyunsaturated etherlipids (PUFA ae) to total amount of monounsaturated fatty acid ether lipids (MUFA ae) and the ratio of total amount of monounsaturated fatty acid ether lipids (MUFA ae) to total amount of saturated fatty acids (SFA).

[14] The method of [13], further comprising measuring the amount of at least one acylcarnitine and/or measuring the amount of at least one sphingomyelin.

[15] The method of [14], wherein the at least one acylcarnitine is selected from those included in Table 2 of the specification and/or the at least one sphingomyelin is selected from those included in Table 4 of the specification, respectively.

[16] The method according to any one of [4] to [15], wherein the measurement is based on a quantitative analytical method, preferably chromatography, spectroscopy, and mass spectrometry.

[17]. The method according to [16], wherein chromatography comprises GC, CE, LC, HPLC, and UHPLC; spectroscopy comprises UV/Vis, IR, and NMR; and mass analyzers/spectrometry comprises ESI or APCI-QqQ, ESI or APCI-QqTOF, MALDI-QqQ, MALDI-QqTOF, and MALDI-TOF-TOF.

[18] The method according to [17], wherein mass analyzers/spectrometry comprises Quadrupole Mass Analyzer, Ion Trap Mass Analyzers, TOP (Time of Flight) Mass Analyzer, Orbitrap mass analyser, Magnetic Sector Mass Analyzer, Electrostatic Sector Mass Analyzer, Ion Cyclotron Resonance (ICR) and combinations of mass analyzers, including single quadrupole (Q) and triple quadrupole (QqQ), QqTOF, TOF-TOF, Q-Orbitrap.

BRIEF DESCRIPTION OF THE FIGURES

In the annex of the specification reference is made to the following FIGS. 1-9. These demonstrate examples according to the invention of the increase or decrease of a metabolic biomarker in patient's suffering from HIV compared to non-HIV infected patients as control.

FIG. 3.1: ROC curve multivariate analysis demonstrate the enormous discriminative capacities of the test even after 1000 permutations.

FIG. 3.2: Metabolites used in the ROC analysis of FIG. 3.1.

FIG. 4A1: View of the predicted class probabilities to discriminate HIV from Controls.

FIG. 4A2: View of the predicted class probabilities to discriminate HIV from Controls.

FIG. 5A: The ACADM deficiency observed in HIV patients is present at the same levels in all groups and did not change significantly over time (p=1.3892E-9, −log 10(p)=8.8572, FDR=1.9757E-8)

FIG. 7B: Ratio of Total PC ae to Total PC demonstrates that in the immunologic response group the production of ether lipids is significantly down regulated one year after the first visit. The opposite is happening in the non-immunologic response group (p=3.592E-5; −log(10(p)=4.4447, FDR=3.1709E-4) (ANOVA PostHoc) (abbreviations as above).

DESCRIPTION OF THE PREFERRED EMBODIMENTS

Figure 1:
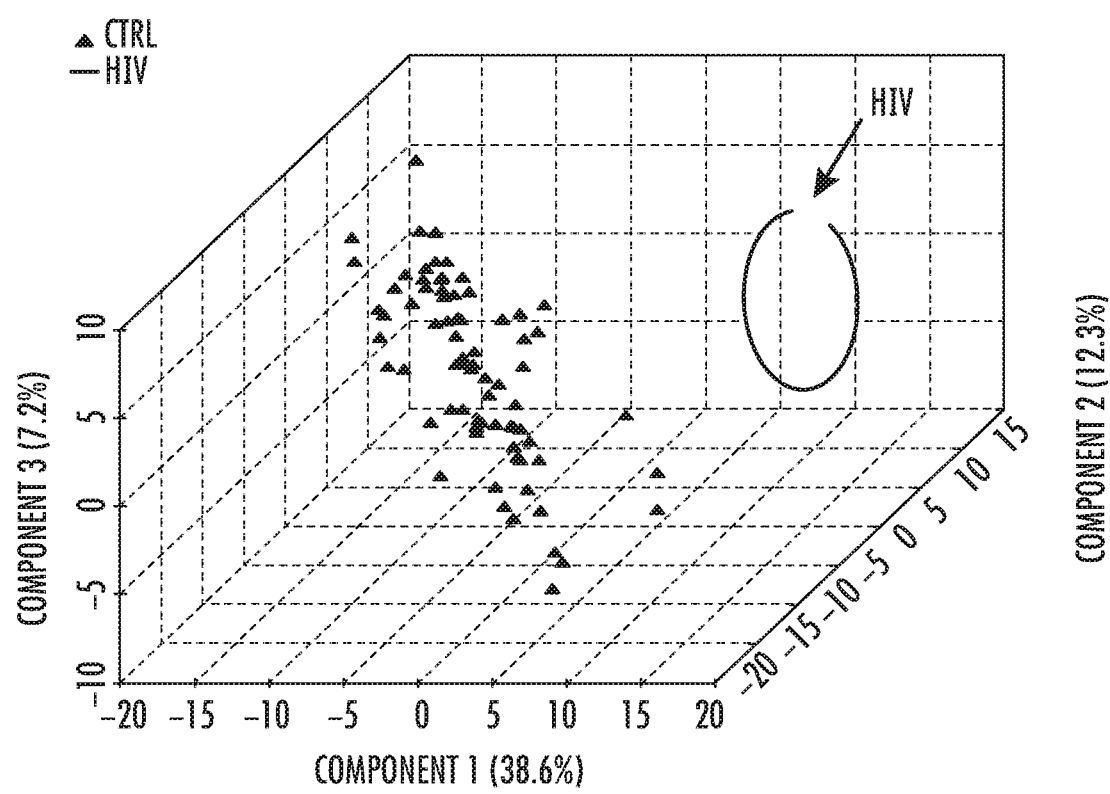
FIG. 1: PLS-DA analysis showing the clear discrimination between HIV patients in accute and chronic stages, with and without detectable Viral Load compared to controls including HIV-negative breast cancer cases as part of controls.

By employing the specific (set of) biomarkers and the methods according to the present invention it has become possible to more properly and reliably assess HIV. "Assessing" in the sense of the present invention means screening of HIV infection and/or diagnosing the HIV infection in patients, predicting immunologic response to antiretroviral therapy and prognosis of HIV disease progression, and monitoring HIV disease activity, in particular the detection and marking of the disease at the different stages and monitoring the progression of the disease.

The present invention makes it possible to screen HIV patients and diagnose HIV in an improved manner and at an early stage of the disease and allows a more sensitive prediction of disease progression. The present invention further allows for prediction of a patient's response to ART and discriminating between immunological groups of patients. In fact, the biomarkers according to the invention are easily detectable in biological samples, in particular in blood, and their level is consistently related to the degree of HIV.

In general, a biomarker is a valuable tool due to the possibility to distinguish two or more biological states from one another, working as an indicator of a normal biological process, a pathogenic process or as a reaction to a pharmaceutical intervention. A metabolite is a low molecular compound (<1 kDa), smaller than most proteins, DNA and other macromolecules. Small changes in activity of proteins result in big changes in the biochemical reactions and their metabolites (=metabolic biomarker, looking at the body's metabolism), whose concentrations, fluxes and transport mechanisms are sensitive to diseases and drug intervention. This enables getting an individual profile of physiological and pathophysiological substances, reflecting both genetics and enviromental factors like nutrition, physical activity, gut microbal and medication. Thus, a metabolic biomarker gives more comprehensive information than for example a protein or hormone, which are biomarkers, but not metabolic biomarkers.

In view thereof, the term metabolic biomarker ("biomarker") as used herein is defined to be a compound suitable as an indicator of the state of HIV being a metabolite or metabolic compound occurring during metabolic processes in the mammalian body. The terms "biomarker", "metabolic biomarker" and "metabolite" are in general used synonymously in the context of the present invention. In particular, the presence of a certain amount (typically mass % or mol % preferably mol %) of a metabolite and/or the ratio (of an amount) of a metabolite with respect to (the amount of) another metabolite is used as "biomarker" and is used in the present invention in the uses and methods as described herein. Thus, the term metabolic biomarker or biomarker is intended to also comprise ratios between two or more metabolites/biomarkers. Thus, the term "biomarker" may also encompass the ratio of the amount of two or more metabolites.

The metabolic biomarker (set) measured according to the present invention mandatorilly comprises the following classes of metabolites (i.e. analytes): amino acids and biogenic amines, acylcarnitines, hexoses, sphingolipids, and glycerophospholipids. Lipids are preferably arachidonic ether lipids, preferably those having more than 38 carbon atoms per molecule. The definitions of these classes are known to the skilled person, however, preferred members of these classes are summarized in Tables 1-5 hereinbelow. Moreover, biogenic amities are understood as a group of naturally occurring biologically active compounds derived by enzymatic decarboxylation of the natural amino acids. A biogenic substance is a substance provided by life processes, and the biogenic amines contain an amine group.

It has surprisingly been found that measuring a set of biomarkers comprising these classes of metabolites allows screening for and diagnosing HIV in an improved manner and at an early stage of the disease. In particular, it allows a more sensitive prediction of progression of HIV as well as prediction of therapeutic response of the patient to ART.

If one class of metabolites of this group is omitted or if the number thereof is decreased the assessment of HIV becomes less sensitive and less reliable. This particularly applies for the early stages of the disease being not reliably detectable according to known methods using known biomarkers at all. In fact, the measurement of the metabolites described herein at the same time allows a more reliable diagnosis of HIV, preferably with a sensitivity of 100%. Such a fact has neither been described in nor made obvious from the prior art.

The biological sample is obtained from a mammal, preferably from a mouse, a rat, a guinea pig, a dog, a mini-pig, or a human, preferably from a human. The biological sample preferably is a blood sample. The blood sample typically is full blood, serum or plasma, wherein blood plasma is preferred. However, any other biological sample known to the skilled person which allows the measurements according to the present invention is also suitable. Thus, the method according to the invention is an in vitro method.

For the measurement of the metabolite concentrations in the biological sample a quantitative analytical method such as chromatography, spectroscopy, and mass spectrometry is employed, while mass spectrometry is particularly preferred. The chromatography may comprise GC, LC, HPLC, and UPLC; spectroscopy may comprise UV/Vis, IR, and NMR; and mass spectrometry may comprise ESI-QqQ, ESI-QqTOF, MALDI-QqQ, MALDI-QqTOF, and MALDI-TOF-TOF. Preferred is the use of FIA- and HPLC-tandem mass spectrometry. These analytical methods are generally known to the skilled person.

Further preferably, mass analyzers/spectrometry comprise Quadrupole Mass Analyzer, Ion Trap Mass Analyzer, TOF (Time of Flight) Mass Analyzer, Orbitrap mass analyser, Magnetic Sector Mass Analyzer, Electrostatic Sector Mass Analyzer, Ion Cyclotron Resonance (ICR) and combinations of mass analyzers, including single quadrupole (Q) and triple quadrupole (QqQ), QqTOF, TOF-TOF, Q-Orbitrap.

For measuring the metabolite amounts targeted metabolomics is used to quantify the metabolites in the biological sample including the analyte classes of amino acids, biogenic amines, acylcarnitines, hexoses, sphingolipids and glycerophospholipids. Amino acids preferentially include the 20 known proteinogenic amino acids. The quantification is done using in the presence of isotopically labeled internal standards and determined by the methods as described above.

A list of analytes including their abbreviations (BC codes) being suitable as metabolites to be measured according to the invention is indicated in the following Tables. Classification of metabolites by the BC code is as explained in EP 2 284 540 A1 using the following abbreviations:

Acylcarnitinea (C chain length; total number of double bonds) e.g. C14:1

Sphingomyelins (SM chain length:total number of double bonds) e.g. SM 16:0

Phosphatidylcholines (PC)

Monoacylphosphatidylcholines (PC a chain length:total number of doubte bonds) e.g. PC a C 18:2

Diacylphosphatidylcholines (PC aa chain length:total number of double bonds) e.g. PC aa 28:1

Acylalkylphospbatidylcholines (PC ae chain length:total number of double bonds) e.g. PC ae C40:1

Polyunsaturated fatty acid (PUFA)

Monounsaturated fatty acid (MUFA)

Saturated fatty acid (SFA)

TABLE 1

Amino acids and biogenic amines (μM)

| BC code | Analyte |
| --- | --- |
| Ala | Alanine |
| Arg | Arginine |
| Asn | Asparagine |
| Asp | Aspartate |
| Cit | Citrulline |
| Gln | Glutamine |
| Glu | Glutamate |
| Gly | Glycine |
| His | Histidine |
| Ile | Isoleucine |
| Leu | Leucine |
| Lys | Lysine |
| Met | Methionine |
| Orn | Ornithine |
| Phe | Phenylalanine |
| Pro | Proline |
| Ser | Serine |

TABLE 1-continued

Amino acids and biogenic amines (μM)

| BC code | Analyte |
| --- | --- |
| Thr | Threonine |
| Trp | Tryptophane |
| Tyr | Tyrosine |
| Val | Valine |
| Ac-Orn | Acetylornithine |
| ADMA | Asymmetric dimethylarginine |
| SDMA | Symmetric dimethylarginine |
| total DMA | Total dimethylarginine |
| alpha-AAA | alpha-Aminoadipic acid |
| Carnosine | Carnosine |
| Creatinine | Creatinine |
| Histamine | Histamine |
| Kynurenine | Kynurenine |
| Met-SO | Methioninesulfoxide |
| Nitro-Tyr | Nitrotyrosine |
| OH-Pro | Hydroxyproline |
| PEA | Phenylethylamine |
| Putrescine | Putrescine |
| Sarcosine | Sarcosine |
| Serotonin | Serotonin |
| Spermidine | Spermidine |
| Spermine | Spermine |
| Taurine | Taurine |

TABLE 2

Acylcarnitine (μM)

| BC code | Analyte |
| --- | --- |
| C0 | Carnitine |
| C2 | Acetylcarnitine |
| C3 | Propionylcarnitine |
| C3:1 | Propenoylcarnitine |
| C3—OH | Hydroxypropionylcarnitine |
| C4 | Butyrylcarnitine |
| C4:1 | Butenylcarnitine |
| C4—OH (C3-DC) | Hydroxybutyrylcarnitine |
| C5 | Valerylcarnitine |
| C5:1 | Tiglylcarnitine |
| C5:1-DC | Glutaconylcarnitine |
| C5-DC (C6—OH) | Glutarylcarnitine* (Hydroxyhexanoylcarnitine) |
| C5-M-DC | Methylglutarylcarnitine |
| C5—OH (C3-DC-M) | Hydroxyvalerylcarnitine (Methylmalonylcarnitine) |
| C6 (C4:1-DC) | Hexanoylcarnitine (Fumarylcarnitine) |
| C6:1 | Hexenoylcarnitine |
| C7-DC | Pimelylcarnitine |
| C8 | Octanoylcarnitine |
| C9 | Nonaylcarnitine |
| C10 | Decanoylcarnitine |
| C10:1 | Decenoylcarnitine |
| C10:2 | Decadienylcarnitine |
| C12 | Dodecanoylcarnitine |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1—OH | Hydroxytetradecenoylcarnitine |
| C14:2 | Tetradecadienylcarnitine |
| C14:2—OH | Hydroxytetradecadienylcarnitine |
| C16 | Hexadecanoylcarnitine |
| C16:1 | Hexadecenoylcarnitine |
| C16:1—OH | Hydroxyhexadecenoylcarnitine |
| 16:2 | Hexadecadienylcarnitine |
| 16:2—OH | Hydroxyhexadecadienylcarnitine |
| C16—OH | Hydroxyhexadecanoylcarnitine |
| C18 | Octadecanoylcarnitine |
| C18:1 | Octadecenoylcarnitine |
| C18:1—OH | Hydroxyoctadecenoylcarnitine |
| C18:2 | Octadecadienylcarnitine |
| C10:1 | Decenoylcarnitine |
| C10:2 | Decadienylcarnitine |
| C12 | Dodecanoylcarnitine |

TABLE 2-continued

Acylcarnitine (μM)

| BC code | Analyte |
| --- | --- |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1—OH | Hydroxytetradecenoylcarnitine |
| C14:2 | Tetradecadienylcarnitine |
| C14:2—OH | Hydroxytetradecadienylcarnitine |
| C16 | Hexadecanoylcarnitine |

TABLE 3

Hexoses (mM)

| BC code | Analyte |
| --- | --- |
| H1 | Hexose |

TABLE 4

Sphingolipids (mM)

| BC code | Analyte |
| --- | --- |
| SM (OH) C14:1 | Hydroxysphingomyelin with acyl residue sum C14:1 |
| SM (OH) C16:1 | Hydroxysphingomyelin with acyl residue sum C16:1 |
| SM (OH) C22:1 | Hydroxysphingomyelin with acyl residue sum C22:1 |
| SM (OH) C22:2 | Hydroxysphingomyelin with acyl residue sum C22:2 |
| SM (OH) C24:1 | Hydroxysphingomyelin with acyl residue sum C24:1 |
| SM C16:0 | sphingomyelin with acyl residue sum C16:0 |
| SM C16:1 | sphingomyelin with acyl residue sum C16:1 |
| SM C18:0 | sphingomyelin with acyl residue sum C18:0 |
| SM C18:1 | sphingomyelin with acyl residue sum C18:1 |
| SM C20:2 | sphingomyelin with acyl residue sum C20:2 |
| SM C22:3 | sphingomyelin with acyl residue sum C22:3 |
| SM C24:0 | sphingomyelin with acyl residue sum C24:0 |
| SM C24:1 | sphingomyelin with acyl residue sum C24:1 |
| SM C26:0 | sphingomyelin with acyl residue sum C26:0 |
| SM C26:1 | sphingomyelin with acyl residue sum C26:1 |

TABLE 5

Glycerophospholipids (mM)

| BC code | Analyte |
| --- | --- |
| lysoPC a C14:0 | Lysophosphatidylcholine with acyl residue C14:0 |
| lysoPC a C16:0 | Lysophosphatidylcholine with acyl residue C16:0 |
| lysoPC a C16:1 | Lysophosphatidylcholine with acyl residue C16:1 |
| lysoPC a C17:0 | Lysophosphatidylcholine with acyl residue C17:0 |
| lysoPC a C18:0 | Lysophosphatidylcholine with acyl residue C18:0 |
| lysoPC a C18:1 | Lysophosphatidylcholine with acyl residue C18:1 |
| lysoPC a C18:2 | Lysophosphatidylcholine with acyl residue C18:2 |
| lysoPC a C20:3 | Lysophosphatidylcholine with acyl residue C20:3 |
| lysoPC a C20:4 | Lysophosphatidylcholine with acyl residue C20:4 |
| lysoPC a C24:0 | Lysophosphatidylcholine with acyl residue C24:0 |
| lysoPC a C26:0 | Lysophosphatidylcholine with acyl residue C26:0 |
| lysoPC a C26:1 | Lysophosphatidylcholine with acyl residue C26:1 |
| lysoPC a C28:0 | Lysophosphatidylcholine with acyl residue C28:0 |
| lysoPC a C28:1 | Lysophosphatidylcholine with acyl residue C28:1 |
| PC aa C24:0 | Phosphatidylcholine with diacyl residue sum C24:0 |
| PC aa C26:0 | Phosphatidylcholine with diacyl residue sum C26:0 |
| PC aa C28:1 | Phosphatidylcholine with diacyl residue sum C28:1 |
| PC aa C30:0 | Phosphatidylcholine with diacyl residue sum C30:0 |
| PC aa C30:2 | Phosphatidylcholine with diacyl residue sum C30:2 |
| PC aa C32:0 | Phosphatidylcholine with diacyl residue sum C32:0 |
| PC aa C32:1 | Phosphatidylcholine with diacyl residue sum C32:1 |
| PC aa C32:2 | Phosphatidylcholine with diacyl residue sum C32:2 |
| PC aa C32:3 | Phosphatidylcholine with diacyl residue sum C32:3 |
| PC aa C34:1 | Phosphatidylcholine with diacyl residue sum C34:1 |
| PC aa C34:2 | Phosphatidylcholine with diacyl residue sum C34:2 |
| PC aa C34:3 | Phosphatidylcholine with diacyl residue sum C34:3 |
| PC aa C34:4 | Phosphatidylcholine with diacyl residue sum C34:4 |
| PC aa C36:0 | Phosphatidylcholine with diacyl residue sum C36:0 |
| PC aa C36:1 | Phosphatidylcholine with diacyl residue sum C36:1 |
| PC aa C36:2 | Phosphatidylcholine with diacyl residue sum C36:2 |
| PC aa C36:3 | Phosphatidylcholine with diacyl residue sum C36:3 |
| PC aa C36:4 | Phosphatidylcholine with diacyl residue sum C36:4 |
| PC aa C36:5 | Phosphatidylcholine with diacyl residue sum C36:5 |
| PC aa C36:6 | Phosphatidylcholine with diacyl residue sum C36:6 |
| PC aa C38:0 | Phosphatidylcholine with diacyl residue sum C38:0 |
| PC aa C38:1 | Phosphatidylcholine with diacyl residue sum C38:1 |
| PC aa C38:3 | Phosphatidylcholine with diacyl residue sum C38:3 |
| PC aa C38:4 | Phosphatidylcholine with diacyl residue sum C38:4 |
| PC aa C38:5 | Phosphatidylcholine with diacyl residue sum C38:5 |
| PC aa C38:6 | Phosphatidylcholine with diacyl residue sum C38:6 |
| PC aa C40:1 | Phosphatidylcholine with diacyl residue sum C40:1 |
| PC aa C40:2 | Phosphatidylcholine with diacyl residue sum C40:2 |
| PC aa C40:3 | Phosphatidylcholine with diacyl residue sum C40:3 |
| PC aa C40:4 | Phosphatidylcholine with diacyl residue sum C40:4 |
| PC aa C40:5 | Phosphatidylcholine with diacyl residue sum C40:5 |
| PC aa C40:6 | Phosphatidylcholine with diacyl residue sum C40:6 |
| PC aa C42:0 | Phosphatidylcholine with diacyl residue sum C42:0 |
| PC aa C42:1 | Phosphatidylcholine with diacyl residue sum C42:1 |
| PC aa C42:2 | Phosphatidylcholine with diacyl residue sum C42:2 |
| PC aa C42:4 | Phosphatidylcholine with diacyl residue sum C42:4 |
| PC aa C42:5 | Phosphatidylcholine with diacyl residue sum C42:5 |
| PC aa C42:6 | Phosphatidylcholine with diacyl residue sum C42:6 |
| PC ae C30:0 | Phosphatidylcholine with acyl-alkyl residue sum C30:0 |
| PC ae C30:1 | Phosphatidylcholine with acyl-alkyl residue sum C30:1 |
| PC ae C30:2 | Phosphatidylcholine with acyl-alkyl residue sum C30:2 |
| PC ae C32:1 | Phosphatidylcholine with acyl-alkyl residue sum C32:1 |
| PC ae C32:2 | Phosphatidylcholine with acyl-alkyl residue sum C32:2 |
| PC ae C34:0 | Phosphatidylcholine with acyl-alkyl residue sum C34:0 |
| PC ae C34:1 | Phosphatidylcholine with acyl-alkyl residue sum C34:1 |
| PC ae C34:2 | Phosphatidylcholine with acyl-alkyl residue sum C34:2 |
| PC ae C34:3 | Phosphatidylcholine with acyl-alkyl residue sum C34:3 |
| PC ae C36:0 | Phosphatidylcholine with acyl-alkyl residue sum C36:0 |
| PC ae C36:1 | Phosphatidylcholine with acyl-alkyl residue sum C36:1 |
| PC ae C36:2 | Phosphatidylcholine with acyl-alkyl residue sum C36:2 |
| PC ae C36:3 | Phosphatidylcholine with acyl-alkyl residue sum C36:3 |
| PC ae C36:4 | Phosphatidylcholine with acyl-alkyl residue sum C36:4 |
| PC ae C36:5 | Phosphatidylcholine with acyl-alkyl residue sum C36:5 |
| PC ae C38:0 | Phosphatidylcholine with acyl-alkyl residue sum C38:0 |
| PC ae C38:1 | Phosphatidylcholine with acyl-alkyl residue sum C38:1 |
| PC ae C38:2 | Phosphatidylcholine with acyl-alkyl residue sum C38:2 |
| PC ae C38:3 | Phosphatidylcholine with acyl-alkyl residue sum C38:3 |
| PC ae C38:4 | Phosphatidylcholine with acyl-alkyl residue sum C38:4 |
| PC ae C38:5 | Phosphatidylcholine with acyl-alkyl residue sum C38:5 |
| PC ae C38:6 | Phosphatidylcholine with acyl-alkyl residue sum C38:6 |
| PC ae C40:1 | Phosphatidylcholine with acyl-alkyl residue sum C40:1 |
| PC ae C40:2 | Phosphatidylcholine with acyl-alkyl residue sum C40:2 |
| PC ae C40:3 | Phosphatidylcholine with acyl-alkyl residue sum C40:3 |
| PC ae C40:4 | Phosphatidylcholine with acyl-alkyl residue sum C40:4 |
| PC ae C40:5 | Phosphatidylcholine with acyl-alkyl residue sum C40:5 |
| PC ae C40:6 | Phosphatidylcholine with acyl-alkyl residue sum C40:6 |
| PC ae C42:0 | Phosphatidylcholine with acyl-alkyl residue sum C42:0 |
| PC ae C42:1 | Phosphatidylcholine with acyl-alkyl residue sum C42:1 |
| PC ae C42:2 | Phosphatidylcholine with acyl-alkyl residue sum C42:2 |
| PC ae C42:3 | Phosphatidylcholine with acyl-alkyl residue sum C42:3 |
| PC ae C42:4 | Phosphatidylcholine with acyl-alkyl residue sum C42:4 |
| PC ae C42:5 | Phosphatidylcholine with acyl-alkyl residue sum C42:5 |
| PC ae C44:3 | Phosphatidylcholine with acyl-alkyl residue sum C44:3 |
| PC ae C44:4 | Phosphatidylcholine with acyl-alkyl residue sum C44:4 |
| PC ae C44:5 | Phosphatidylcholine with acyl-alkyl residue sum C44:5 |
| PC ae C44:6 | Phosphatidylcholine with acyl-alkyl residue sum C44:6 |

Further preferred embodiments of the present invention are described in the following. However, their combination with features described further above is not intended to be excluded.

Screening/Diagnosis of Patients

In a preferred embodiment, the biomarkers and biomarker sets of the present invention are used for screening of patients potentially suffering from HIV and diagnosing HIV in these patients. It has surprisingly been found in the present invention that the biomarkers and biomarker sets as described herein are particularly useful for fast, easy and highthroughput screening and/or diagnosing of a large number of patients with improved accuracy of results. Thus, in this preferred embodiment assessing comprises screening of and diagnosis of HIV infection in a mammalian subject, preferably in a human. In particular, it is possible to screen/diagnose the disease in subjects independent from the activity of the virus, i.e. asymptomatically.

Thus, in a preferred embodiment, the invention is directed to the Use of a combination of metabolites contained in a blood sample, comprising at least one acylcarnitine (AC) and at least one sphingomyelin (SM) as a biomarker set for screening and/or diagnosing HIV.

The present invention is further directed to a method for screening and/or diagnosing HIV in a mammalian subject, the method comprising measuring in a blood sample obtained from the subject the amount of at least one acylcarnitine (AC) and at least one sphingomyelin (SM).

In particular it is possible to discriminate between subjects suffering from HIV and healthy controls, i.e. non-HIV infected subjects, by using the above combination of metabolites.

Preferably, the at least one acylcarnitine is selected from those included in Table 2 shown above. Further preferably, the at least one sphingomyelin is selected from those included in Table 4 above. Further preferably, the at least one acylcarnitine is selected from glutaconylcarnitine, methylglutarylcarnitine, octanoylcarnitine, decanoylcarnitine, and dodecanoylcarnitine.

Further preferably, the method comprises measuring the amount of at least one biogenic amine and/or of at least one phosphatidylcholine.

Further preferably, the method comprises measuring the amount of at least one sphingomyelin, in particular measuring the ratio of amount of hydroxysphingomyelin with acyl residue sum of C24:1 (SM(OH) C24:1) to the amount of sphingomyelin with acyl residue sum of C1.6:0 (SM C16:0)

Measuring additional amounts of metabolites and/or additional ratios of metabolites as listed in Tables 6 and 7 below will further improve the accuracy of discrimination between these subjects and thus will improve accuracy of screening and/or diagnosis results.

TABLE 6

Preferred metabolites used for screening and diagnosis of HIV in subjects (BC codes as in Tables 1-5):

| BC code | Correlation with HIV | T-test | p-Value | FDR |
|---|---|---|---|---|
| C5-M-DC | 0.87409 | 18.872 | 0.0 | 0.0 |
| C5:1-DC | 0.89539 | 21.09 | 0.0 | 0.0 |
| SM C24:1 | −0.95188 | −32.575 | 2.5393E−58 | 1.9552E−56 |
| Tot SMs | −0.95159 | −32.472 | 3.4828E−58 | 2.0113E−56 |
| C12-DC | −0.95012 | −31.952 | 1.7345E−57 | 8.0133E−56 |
| SM C24:0 | −0.9485 | −31.403 | 9.6892E−57 | 3.7303E−55 |
| DOPA | −0.94487 | −30.265 | 3.6992E−55 | 1.2207E−53 |
| SM (OH) C22:2 | −0.94426 | −30.082 | 6.7198E−55 | 1.9404E−53 |
| SM C16:1 | −0.93958 | −28.787 | 4.9442E−53 | 1.269E−51 |
| SM (OH) C22:1 | −0.93507 | −27.668 | 2.2957E−51 | 5.3031E−50 |
| SM C16:0 | −0.93453 | −27.541 | 3.5697E−51 | 7.4963E−50 |
| SM C18:0 | −0.93053 | −26.65 | 8.3282E−50 | 1.6032E−48 |
| SM C18:1 | −0.92956 | −26.444 | 1.7486E−49 | 3.1072E−48 |
| SM (OH) C16:1 | −0.91534 | −23.841 | 2.9075E−45 | 4.7973E−44 |
| SM (OH) C24:1 | −0.90472 | −22.274 | 1.4376E−42 | 2.2139E−41 |
| SM (OH) C14:1 | −0.90051 | −21.72 | 1.3825E−41 | 1.996E−40 |
| SM C20:2 | −0.89379 | −20.902 | 4.1646E−40 | 5.6589E−39 |
| SM C26:1 | −0.86386 | −17.986 | 1.5307E−34 | 1.9644E−33 |

TABLE 6-continued

Preferred metabolites used for screening and diagnosis of HIV in subjects (BC codes as in Tables 1-5):

| BC code | Correlation with HIV | T-test | p-Value | FDR |
|---|---|---|---|---|
| Nitro-Tyr | −0.7976 | −13.869 | 6.698E−26 | 8.1434E−25 |
| C12 | −0.70686 | −10.481 | 3.0712E−18 | 3.5473E−17 |
| C8:1 | −0.70251 | −10.353 | 6.0361E−18 | 6.6397E−17 |
| PC ae C30:2 | −0.66854 | −9.4285 | 7.992E−16 | 8.3916E−15 |
| Sarcosine | −0.66406 | −9.1351 | 1.4523E−15 | 1.4586E−14 |
| C5—OH (C3-DC-M) | −0.64923 | −8.9525 | 9.7584E−15 | 9.3924E−14 |
| PC ae C30:0 | −0.64339 | −8.8146 | 2.0084E−14 | 1.8558E−13 |

TABLE 7

Preferred ratios of metabolites used for screening and diagnosis of HIV in subjects (BC codes as in Tables 1-5, AUC: area under the receiver operating characteristic (ROC) curve):

| Metabolite Ratios | AUC | p-Value |
|---|---|---|
| C5-M-DC/Total SMs | 1.0 | 2.7246E−63 |
| C5-M-DC/Total OH-SMs | 1.0 | 1.2081E−62 |
| C5-M-DC/Total Non-OH SMs | 1.0 | 1.074E−62 |
| C5-M-DC/SFA (SM) | 1.0 | 9.1734E−62 |
| C5-M-DC/MUFA (SM) | 1.0 | 4.6149E−64 |
| C5-M-DC/PUFA (SM) | 1.0 | 1.9734E−63 |
| C5:1-DC/C12-DC | 1.0 | 2.4417E−61 |
| C5:1-DC/Total SMs | 1.0 | 5.9247E−68 |
| C5:1-DC/Total OH-SMs | 1.0 | 2.1547E−64 |
| C5:1-DC/Total Non-OH SMs | 1.0 | 6.0825E−68 |
| C5:1-DC/SFA (SM) | 1.0 | 1.2281E−66 |
| C5:1-DC/MUFA (SM) | 1.0 | 1.1064E−68 |
| C5:1-DC/PUFA (SM) | 1.0 | 7.2444E−66 |
| Total SMs/PUFA PCs aa | 1.0 | 6.4861E−62 |
| Total Non-OH SMs/PUFA PCs aa | 1.0 | 4.9571E−60 |
| MUFA (SM)/PUFA PCs ae | 1.0 | 2.641E−60 |
| MUFA (SM)/PUFA PCs aa | 1.0 | 4.07E−63 |
| MUFA (SM)/Non ARAC PC aa | 1.0 | 8.6339E−61 |
| PUFA (SM)/PUFA PCs aa | 1.0 | 7.2335E−62 |

Most preferably, the metabolites are selected from those listed in Table 8 below.

TABLE 8

Further preferred metabolites used for screening and diagnosis of HIV in subjects (BC codes as in Tables 1-5):

| BC code | AUC | p-Value |
|---|---|---|
| Total Non-OH SMs | 1.0 | 1.5679E−53 |
| MUFA (SM) | 1.0 | 6.8445E−55 |
| DOPA | 1.0 | 1.4394E−42 |
| Total SMs | 1.0 | 8.6517E−54 |
| PUFA (SM) | 1.0 | 2.4587E−51 |
| C12-DC | 1.0 | 1.7105E−53 |
| Total OH-SMs | 1.0 | 3.3558E−49 |
| SFA (SM) | 1.0 | 1.4079E−51 |
| C5-M-DC | 0.99963 | 4.5771E−41 |
| C5:1-DC | 0.99963 | 4.358E−45 |
| Nitro-Tyr | 0.94595 | 8.7656E−21 |

Optionally, the method comprises the further step of identifying on the basis of the amounts and ratios measured for the respective biomarkers and biomarker ratios those subjects suffering from HIV and further preferably treating HIV in these subjects by ART, such as HAART.

As the method of this embodiment can be performed from blood samples, the method greatly increases the subject's compliance compared to prior art screening technique. In particular, the method greatly increases reliability and sensitivity of the screening results, in particular reduces the number of false positive and false negative results, and is less time consuming, and thus can be performed with a high number of patients.

Prediction of Immunologic Response to Antiretrovitral Therapy and HIV Prognosis

In another preferred embodiment, the biomarkers and biomarker sets of the present invention are used for predicting whether a patient suffering from HIV is likely to respond to antiretroviral therapy (ART), e.g. high active antiretroviral therapy (HAART). In this embodiment, the HIV patient is typically a patient that has not been subjected to HIV treatment, preferably a patient that has not been subjected to HIV treatment by ART. Thus, the biomarkers and biomarker sets of the present invention are used for predicting whether a patient suffering from HIV is likely to respond to antiretroviral therapy (ART) before starting the therapy.

In particular, it can be discriminated between subjects with good response (good prognosis) and subjects with worse response (worse prognosis). Typically, subject with good prognosis comprise elite controllers (EC) and immunologic responder (IR), whereas subject with worse response comprise immunologic non-responders (INR) and rapid progressors (RP).

Elite controllers are HIV-infected patients capable of controlling virus replication at a level of <50 copies/ml for at least one year without the use of HAART.

Immunologic responders are patients that are characterized by an effective response with respect to CD4+ T and HIV viral load counts, i.e. have undetectable viral load (viremia) and high levels of CD4+ T cells even after long periods of HAART.

Immunologic non-responders are patients that are characterized by a discordant and ineffective response with respect to CD4+ T and HIV viral load counts, i.e. have undetectable viral load (viremia) but persist with low levels of CD4+ T cells even after long periods of HAART.

Slow progressors are HIV-infected patients that maintain stable levels of CD4+ T cells and that remain asymptomatic without the use of HAART.

Thus, in a preferred embodiment, the invention is directed to the use of a combination of metabolites described in the following for predicting whether a mammalian subject suffering from HIV is likely to respond to ART, e.g. HAART.

In particular, the present invention is further directed to the use of a combination of metabolites contained in a blood sample, comprising at least one phosphatidylcholine comprising at least one acyl-alkyl group in the molecule (PC ae), and at least two amino acids as a biomarker set for prediction of immunologic response of a mammalian subject to antiretroviral therapy and/or prognosis of disease progression. In a further embodiment, the present invention is directed to a method for prediction of immunologic response of a mammalian subject to antiretroviral therapy and/or prognosis of HIV disease progression, the method comprising measuring in a blood sample obtained from the subject the amount of at least one phosphatidylcholine with at least one acyl-alkyl group in the molecule (PC ae) and at least two amino acids.

Preferably, the at least one phosphatidylcholine with at least one acyl-alkyl group in the molecule (PC ae) is selected from those included in Table 5 of the specification.

The at least two amino acids are preferably selected from proteinogenic amino acids, most preferably selected from Glu, Tyr and Phe. A preferred combination of amino acids is Tyr and Phe.

Further preferably, the method comprises measuring the amount of at least one acylcarnitine. The at least one acylcarnitine is preferably selected from those included in Table 2 of the specification.

Most preferably, the the method comprises measuring in the blood sample the ratio of a) total AC-DC/C3-OH, b) Tyr/Phe/PC ae C38:4, c) Tyr/Phe/PC ae C40:6, d) C3-OH/C14:2-OH, and e) Tyr/Phe/Sum Arac PC ae.

It was surprisingly found in the present invention that predicting therapeutic response to ART using the above combination of ratios of metabolites was more reliable and effective than with the prior art methods.

In addition, it has surprisingly been found in the present invention that it is possible to discriminate between subgroups of patients and predicting the immunologic response to ART on the basis of their metabolite signature. Thus, it can be discriminated between the immunologic subtypes of elite controllers (EC) and immunologic respondents (IR) versus the group of rapid progressors (RP) and immunologic non-respondents (NIR), on the basis of the metabolic biosignature of HIV disease in these patients. Discrimination between these immunological groups of patients can further increase prediction accuracy of therapeutic response to ART, and thus can greatly improve therapeutic success. Particularly, the Good Prognosis Group is composed of patients from elite controllers and immunological responders, which are the patients with the highest chance of of long time survival. The Worse Prognosis Group is composed of patients that either develop AIDS in less than 1 or 2 years (Rapid Progressors) or did not show immunity recovering, as revealed by lower CD4/CD8 levels, after antiretroviral treatment. In particular, it is possible to receive an accurst prognosis of the disease progression and immunologic response independent from the disease state at time of performing the methods of the present invention.

Measuring additional amounts of metabolites and/or additional ratios of metabolites as listed in Tables 9 and 10 will further improve the accuracy of discrimination between these immunological groups and thus will improve prediction accuracy of therapeutic response to ART, such as HAART.

TABLE 9

Metabolites that discriminate elite controllers (ER) from the immunological groups NIR, IR and RP

| BC code | AUC | P-value |
| --- | --- | --- |
| Met | 0.94643 | 0.017092 |
| Gln | 0.91071 | 0.031296 |
| Tyr | 0.91071 | 0.0053004 |
| C6:1 | 0.91071 | 0.026148 |
| Glyco/Gluta | 0.89286 | 0.042728 |
| alpha-AAA | 0.89286 | 0.03133 |
| C3 | 0.89286 | 0.011261 |
| Essential AA | 0.875 | 0.014459 |
| Lys | 0.875 | 0.050259 |
| Trp | 0.875 | 0.017911 |

TABLE 10

Metabolites Ratios that discriminate elite controllers
(ER) from the immunological groups NIR, IR and RP

| BC code | AUC | P-value |
|---|---|---|
| Glu/Tyr | 1.0 | 7.6051E-5 |
| Tyr/PC aa C40:1 | 1.0 | 2.162E-4 |
| Tyr/PC ae C40:4 | 1.0 | 2.3559E-5 |
| Tyr/PC ae C40:5 | 1.0 | 7.1624E-5 |
| Tyr/PC ae C42:4 | 1.0 | 1.631E-4 |
| PC aa C36:0/PC aa C42:4 | 1.0 | 1.4343E-5 |
| PC aa C36:0/PC ae C40:3 | 1.0 | 1.3387E-4 |
| PC aa C36:0/PC ae C40:4 | 1.0 | 1.3076E-6 |
| PC aa C36:0/PC ae C44:3 | 1.0 | 2.2717E-4 |
| PC ae C32:2/PC ae C40:4 | 1.0 | 2.2265E-4 |
| PC ae C40:1/PC ae C40:4 | 1.0 | 2.2424E-5 |
| Tyr/PC ae C30:2 | 0.98214 | 2.1209E-4 |
| Tyr/PC ae C42:5 | 0.98214 | 1.3096E-4 |
| PC aa C36:0/PC aa C40:1 | 0.98214 | 2.0831E-4 |
| PC aa C36:0/PC ae C36:1 | 0.98214 | 1.3905E-4 |
| PC aa C36:0/PC ae C38:3 | 0.98214 | 1.1414E-4 |
| PC aa C36:5/PC ae C40:4 | 0.98214 | 6.0499E-5 |
| PC aa C42:2/PC ae C40:4 | 0.96429 | 1.584E-4 |
| Glu/Tyr | 1.0 | 7.6051E-5 |
| Tyr/PC aa C40:1 | 1.0 | 2.162E-4 |
| Tyr/PC ae C40:4 | 1.0 | 2.3559E-5 |

Monitoring of HIV Disease Activity

In addition, it is possible with the above listed metabolites to monitor disease activity of HIV in a patient.

Thus, in a further embodiment, the invention is directed to the use of a combination of metabolites contained in a blood sample, comprising at least the ratio of total amount of arachidonic polyunsaturated etherlipids to total amount of monounsaturated fatty acid ether lipids and the ratio of total amount of monounsaturated fatty acid ether lipids to total amount of saturated fatty acids as a biomarker set for monitoring of HIV activity in a mammalian subject.

In a further embodiment, the invention is directed to a method for monitoring of HIV activity in a mammalian subject, the method comprising measuring in a blood sample obtained from the subject at least the ratio of total amount of arachidonic polyunsaturated etherlipids to total amount of monounsaturated fatty acid ether lipids and the ratio of total amount of monounsaturated fatty acid ether lipids to total amount of saturated fatty acids.

In preferred embodiments the arachidonic polyunsaturated etherlipid is polyunsaturated fatty acid (PUFA) PC ae, the monounsaturated fatty acid ether lipid is monounsaturated fatty acid (MUFA) PC ae, and the saturated fatty acid is saturated fatty acid (SFA) PC ae. Hence, preferred ratios comprise PUFA PC ae/MUFA PCae and/or PUFA PC ae/SFA PC ae.

The method preferably further comprises measuring the amount of at least one acylcarnitine and/or measuring the amount of at least one sphingomyelin.

Further preferably, the at least one acylcarnitine is selected from those included in Table 2 of the specification and/or the at least one sphingomyelin is selected from those included in Table 4 of the specification, respectively.

If one class of metabolites of this group is omitted or if the number thereof is decreased the monitoring of HIV disease activity becomes less sensitive and less reliable. This particularly applies for the early stages of the disease being not reliably detectable according to known methods using known biomarkers at all. In fact, the measurement of the combination of metabolites as described herein at the same time allows a more accurate and more reliable monitoring of HIV activity, typically with a sensitivity of preferably more than 80%, more preferably more than 90%, further more preferably more than 98% and most preferably 100%. Such a fact has neither been described in nor made obvious from the prior art.

Moreover, the biomarkers and biomarker sets of the present invention as described herein allow for a more reliable and accurate monitoring of HIV activity with a specificity of more than 80%, more preferably more than 85%, further more preferably more than 90% and most preferably 100%.

Moreover, the biomarker set of the present invention as described herein allows for a more reliable monitoring of HIV activity with a positive predictive value (PPV) of more than 40%, more preferably more than 50%, further more preferably more than 60% and most preferably more than 80%.

Moreover, the biomarker set of the present invention as described herein allows for a more reliable monitoring of HIV activity with a negative predictive value (NPV) of more than 80%, more preferably more than 90%, further more preferably more than 98% and most preferably 100%.

In a preferred embodiment, the biomarker set of the present invention as described herein allows for a more reliable monitoring of HIV activity with a sensitivity of 100% and a NPV of 100%.

In a more preferred embodiment, the biomarker set of the present invention as described herein allows for a more reliable monitoring of HIV activity with a sensitivity of 100%, a specificity of 85% or more and a NPV of 100%.

In a more preferred embodiment, the biomarker set of the present invention as described herein allows for a more monitoring of HIV activity with a sensitivity of 100%, a specificity of 90% or more, a PPV of 80% or more, and a NPV of 100%.

In the most preferred embodiment, the biomarker set of the present invention as described herein allows for a more reliable monitoring of HIV activity with a sensitivity of 100%, a specificity of 100%, a PPV of 100%, and a NPV of 100%.

In particular, it is possible with the (set of) biomarkers as described herein to not only accurately distinguish between the acute phase of HIV infection, i.e. disease activity characterized with a high viral load, and chronic phase, i.e. the HIV virus continues to reproduce at very low levels, although it is still active, of the infection, but to also gain further insights into the biochemical activity of the disease, such as insights into the levels of biooxidation, mitochondrial function, immunity, lipid metabolism and (or insulin resistance. A typical marker of disease activity and disease progression is the CD4 lymphocyte cell count. Hence, disease activity and disease progression can effectively be determined in the present invention by determining the correlation of the biomarker set as described herein with the CD4 cell count, preferably the ratio of CD4/CD8 cells.

With this knowledge, it is possible to accurately adjust and adapt the patient's therapy, such as adapting dosis of administration of an active agent, or administering alternative active agents on the basis of the knowledge received from measuring the (sets of) biomarkers as described herein. Such a fact has never been achieved before.

Kit

Moreover the invention is also directed to a kit adapted for carrying out the method wherein the kit comprises a device which device contains one or more wells and one or more inserts impregnated with at least one internal standard. Such a device is in detail described in WO 2007/003344 and WO 2007/003343 which applications are both incorporated herein by reference.

The following examples further clarify the present invention without being intended to limit the scope in any way.

EXAMPLES

General Information:
Patients and Methods 37 random samples were analyzed from HIV-infected patients prospective followed at Salo Paulo Aids Research Center Cohort (SPARCC). The latter is a recent HIV-infected patient cohort which aim is to study HIV natural history and its progression to AIDS and is well described elsewhere (Kallas BJID 2004).

SPARCC demographic data, HIV-1 viral load and CD4+ cell count were collected every three months during clinical visits. Samples were analyzed at baseline and one year after follow-up. For immunologic non-respondents and immunologic respondents baseline samples were collected immediately pre-treatment with CD4+ cell counts <350 cells/mm3 and one-year samples were collected exactly at 12 months on treatment visit.

Controls included 11 non HIV-infected healthy individuals matched by age and sex and because similar metabolic changes induced by viral infections can also be observed in cancer cells (Yu et al 2011) 64 non HIV-infected stage III breast cancer patients without previous treatment in control group were included. Identify HIV patients even in the presence of metabolomics confounders represented by advanced stage breast cancer patients (stage 3). Breast cancer controls were used due to the fact that similar metabolic changes induced by viral infections can also be observed in cancer cell (glutaminolysis, ether lipid biosynthesis=sum of arachdonic plasmalogen/plasmalogen phosphatidylcholines). However, in HIV patients the increased lipid biosynthesis was not observed for Sphingomyelins (SM); yet it was brutally down regulated.

Metabolite Measurement

Targeted metabolite profiling, by electrospray ionization (ESI) tandem mass spectrometry (MS/MS), was performed in 37 plasma samples collected at baseline and 1 year of follow-up from patients distributed as: 5 immunological nonresponders, 5 immunological responders, 5 rapid progressors and 5 elite patients as well as 75 controls, on a independent, fee-for-service basis on a quantitative metabolomics platform at Biocrates Life Sciences AG, Innsbruck, Austria.

All metabolomics data was used as received from Biocrates. The experimental metabolomics measurement technique is described in detail by patent US 2007/0004044.

Quantification of the metabolites of the biological sample is achieved by reference to appropriate internal standards and the method has been proven to be in conformance with 21CFR (Code of Federal Regulations) Part 11, which implies proof of reproducibility within a even error range. Concentrations of all analyzed metabolites were reported in µM and results were compared to tumor response rates and tumor intrinsic subtypes.

Metabolite Panel

Metabolite panel is composed by 183 different metabolites of which 40 acylcanitines, 19 proteinogenic aminoacids, ornithine and citrulline, 19 biogenic amines, sum of Hexoses, 76 phosphatidylcholines 14 lyso-phosphatidylcholines and 15 sphingomyelins, as shown in Tables 1-5 above.

Glycerophospholipids are further differentiated with respect to the presence of ester (a) and ether (e) bonds in the glycerol moiety, where two letters (aa=diacyl, ae=acyl-alkyl, ee=dialkyl) denote that two glycerol positions are bound to a fatty acid residue, while a single letter (a=acyl or e=alkyl) indicates the presence of a single fatty acid residue.

Lipid side chain composition is abbreviated as Cx:y, where x denotes the number of carbons in the side chain and y the number of double bonds, E.g. "PC ae C38:1" denotes a plasmalogen/plasmenogen phosphatidylcholine with 33 carbons in the two fatty acid side chains and a single double bond in one of them.

Statistical and Data Analysis

Training cases were used for marker discovery and to identify any clinical variable that might be associated with response by logistic regression analysis. Quantification of metabolite concentrations and quality control assessment was performed with the MetIQ software package (BIOCRATES Life Sciences AG, Innsbruck, Austria). Internal standards serve as the reference for the metabolite concentration calculations. An xls file was then exported, which contained sample names, metabolite names and metabolite concentration with the unit of µmol/L of plasma.

Data was then uploaded to the web-based analytical pipeline MetaboAnalyst 2.0 (www.metaboanalyst.ca) and normalized using MetaboAnalyst's normalization protocols (56) for uni and multivariate analysis, high dimensional feature selection, clustering and supervised classification, functional enrichment as well as metabolic pathway analysis.

Data was also imported to ROCCET (ROC Curve Explorer & Tester) available at http://www.roccet.ca/ROC-CET/ for the generation of uni and multivariate Receiver Operating Characteristic (ROC) curves obtained through Support Vector Machine (SVM), Partial Least Squares-Discriminant Analysis (PLS-DA) and Random Forests. Curves were generated by Monte-Carlo cross validation (MCCV) using balanced subsampling where two thirds (⅔) of the samples were used to evaluate the feature importance.

Significant features were then used to build classification models, which were validated on the ⅓ of the samples that were left out. The same procedure was repeated multiple times to calculate the performance and confidence interval of each model.

Definition of terms:

(1) Up- and down regulation: An up-regulation means an increase in the concentration of a metabolite, e.g. an increase in the rate of at which this biochemical reaction occurs due to for example a change in enzymatic activity. For a down-regulation it's the other way around.

(2) t-test: The t-test is a statistical hypothesis test and the one used is the one integrated in the MarkerView software and is applied to every variable in the table and determines if the mean for each group is significantly different given the standard deviation and the number of samples, e.g. to find out if there is a real difference between the means (averages) of two different groups.

(3) p-value: The p-value is the probability of obtaining a result at least as extreme as the one that was actually observed, assuming that the null hypothesis (the hypothesis of no change or effect) is true. The p-value is always positive and the smaller the value the lower the probability that it is a change occurrence. A p-value of 0.05 or less rejects the null hypothesis at the 5% level, which means that only 5% the time the change is a chance occurrence. This is the level set in our tables.

(4) Log-fold change: Log-fold change is defined as the difference between the average log transformed concentrations in each condition. This is a way of describing how much higher or lower the value is in one group compared to another. For example, a log-fold change of 0.3 is "equivalent" to an exp(0.3)=1.34 fold change increase compared to the control (healthier group). Further, a log-fold change of −0.3 is "equivalent" to a exp(−0.3)=0.74=(1/1.34) fold change increase compared to the control or decrease fold change of 1.34 to the disease.

Results

Differentiation in Between HIV-Infected Individuals, Breast Cancer and Healthy Controls First, PLS-DA analysis was performed showing the clear discrimination between HIV patients (n=37) in accute and chronic stages, with and without detectable viral load compared to 75 controls after 100 permutation rounds. Importantly, the identified discriminative profile was robust enough to identify HIV patients even in the presence of metabolomics confounders represented by 64 advanced stage breast cancer patients (FIG. 1). A heatmap analysis generated from this analysis also demonstrates a perfect discrimination in between these three subgroups described above.

Further, a ROC curve analysis (FIG. 3) was performed to once again to demonstrate the enormous discriminative capacities of the applied test even after 1000 permutations (empirical p-value: p<0.001). Further statistical analyses depicted in FIG. 4 demonstrate that after 2000 permutation rounds the prediction accuracy of our test remained highly significant (p<5e-04).

Descriptive Analysis of Blood Metabolites

Figure 2A:
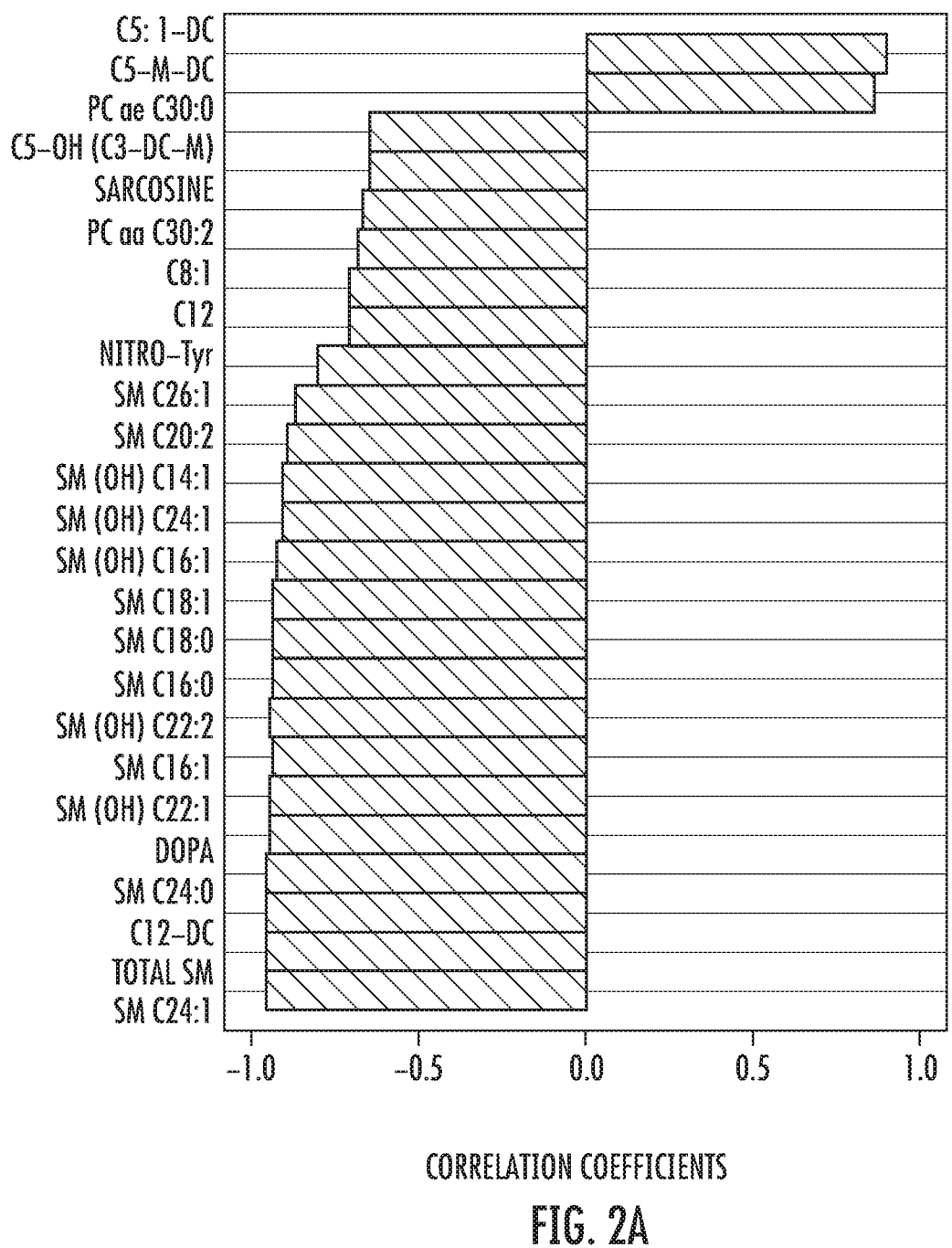
FIG. 2A: Top 25 metabolites correlated (Person r) to HIV showing that HIV is basically related to profound mitochondrial dysfunctions followed by an enormous decrease in Sphingomielins levels.
Figure 2B:
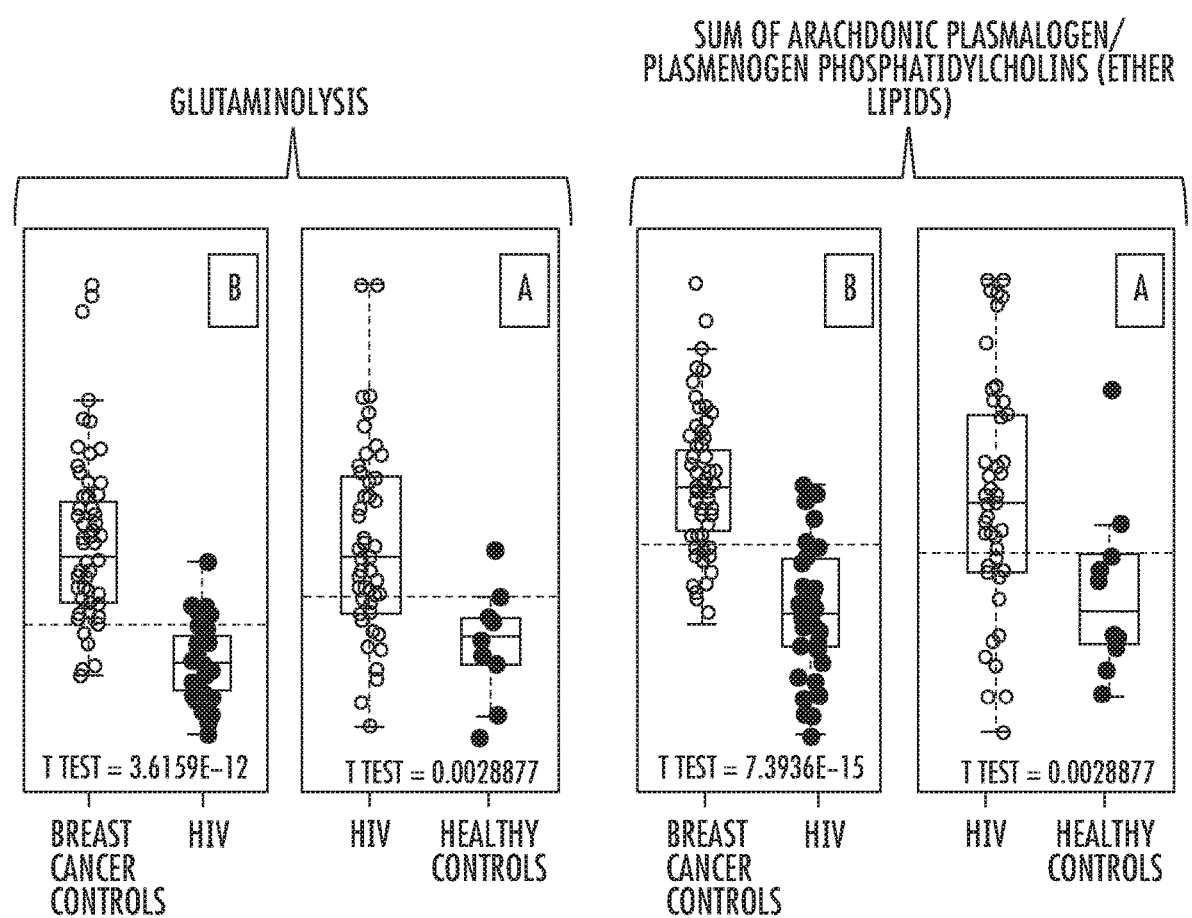
FIG. 2B: Significant increases in glutaminolysis and lipid biosynthesis in HIV and breast cancer patients compared to healthy controls. Viral infections and cancer share similar blood metabolomic changes.

Thirdly, a descriptive analysis of top 25 blood metabolites more correlated with HIV disease was performed using a Pearson's r analysis (Table 6 and FIG. 2). As shown, very low levels of sphyngomielines and dopamine were observed. This finding can also be observed on FIG. 4 where a t-Test analysis based on blood metabolites concentrations from HIV and Controls was performed. Sphingomyelin C24:1 is almost 100 times less concentrated in HIV patients when compared to controls; as expressed on the box plot graphic on FIG. 4A.

Figure 4B:
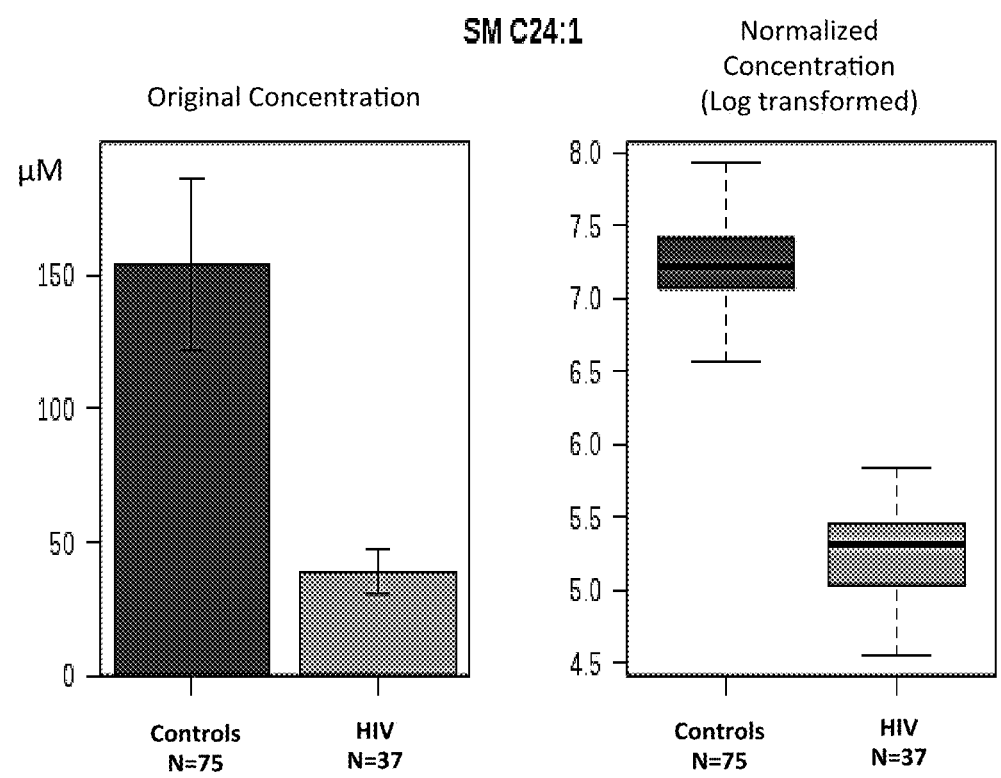
FIG. 4B: T-test analysis based on blood metabolites concentrations up and down-regulated from HIV and Controls. The Figure shows that Sphingomyelin C24:1 is almost 100 times less concentrated in HIV patients when compared to controls.
Figure 4C:
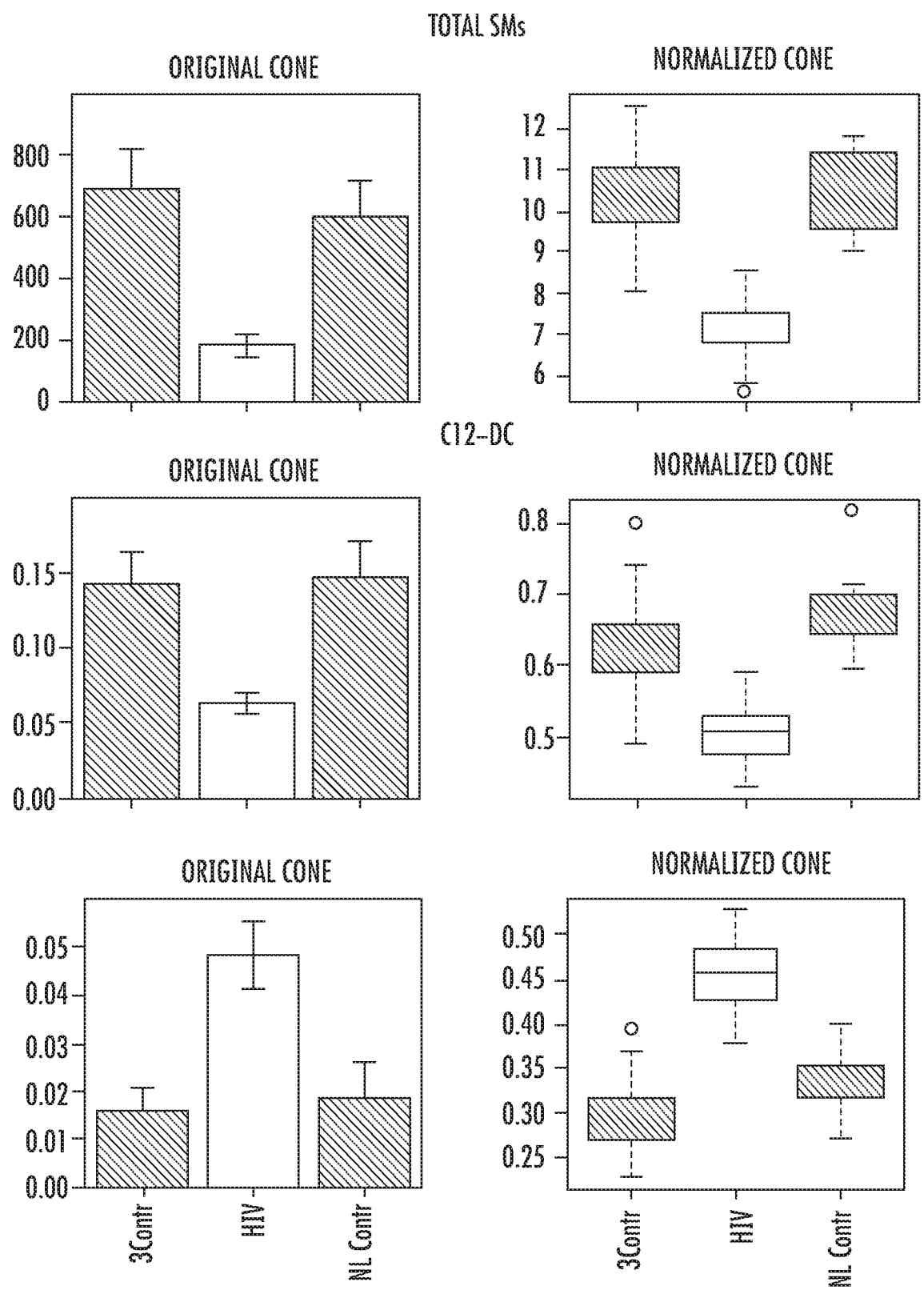
FIG. 4C: Plasma metabolite concentrations of Dodecanedioylcarnitine (C12-DC), Glutaconylcarnitine (C5:1-DC) and Total Sphingomielins (Total SMs) in HIV from Controls.

On the other hand, high levels of acylcanitines C5-M-DC and C5:1-DC were observed at the same time that C12 and C8:1 were down regulated (FIG. 4B). It could be concluded from the severe deregulation in acylcarnitines and sphingomyelins metabolism that HIV infection is followed by functional deficiencies in mitochondrial beta oxidation as well as biosynthesis of sphingolipids.

In order to confirm this conclusion, ratios of certain metabolite concentrations were assembled as a proxy for enzymatic activity related first, to the initial and committing step of beta oxidation catalyzed by the short-, medium- and long-chain acyl-CoA dehydrogenases (ACADS, ACADM, and ACADL, respectively) and second, to the SYNE2 locus due to its relation to SGPP1 (sphingosine-1-phosphate phosphatase 1) activity.

Indeed, experiments in yeast show that sphingosine-1-phosphate stimulates incorporation of palmitate, a substrate for both serine palmitoyltransferase and ceramide synthase, into C16-ceramide, and that SPP-1 (SGPP1 in yeast) expression increased the incorporation of sphingosine into all ceramide acyl chain species, particularly enhancing C16:0, C1.8:0, and C20:0 long-chain ceramides. Additionally, a polymorphism in SGPP1 has been shown, to associate with different sphingomyelin species.

ANOVA statistical results confirmed that HIV infection compared to healthy controls, is followed first, by a significant descent in mitochondrial function as revealed by the important fall in the medium-chain acyl-CoA dehydrogenase (ACADM) function in all 4 groups of patients at baseline and after 1 year follow-up (Ratio C12/C10, p=1.3892E-9, −log 10(p)=8.8572, FDR=1.9757E-8) (FIG. 5A).

Figure 5B:
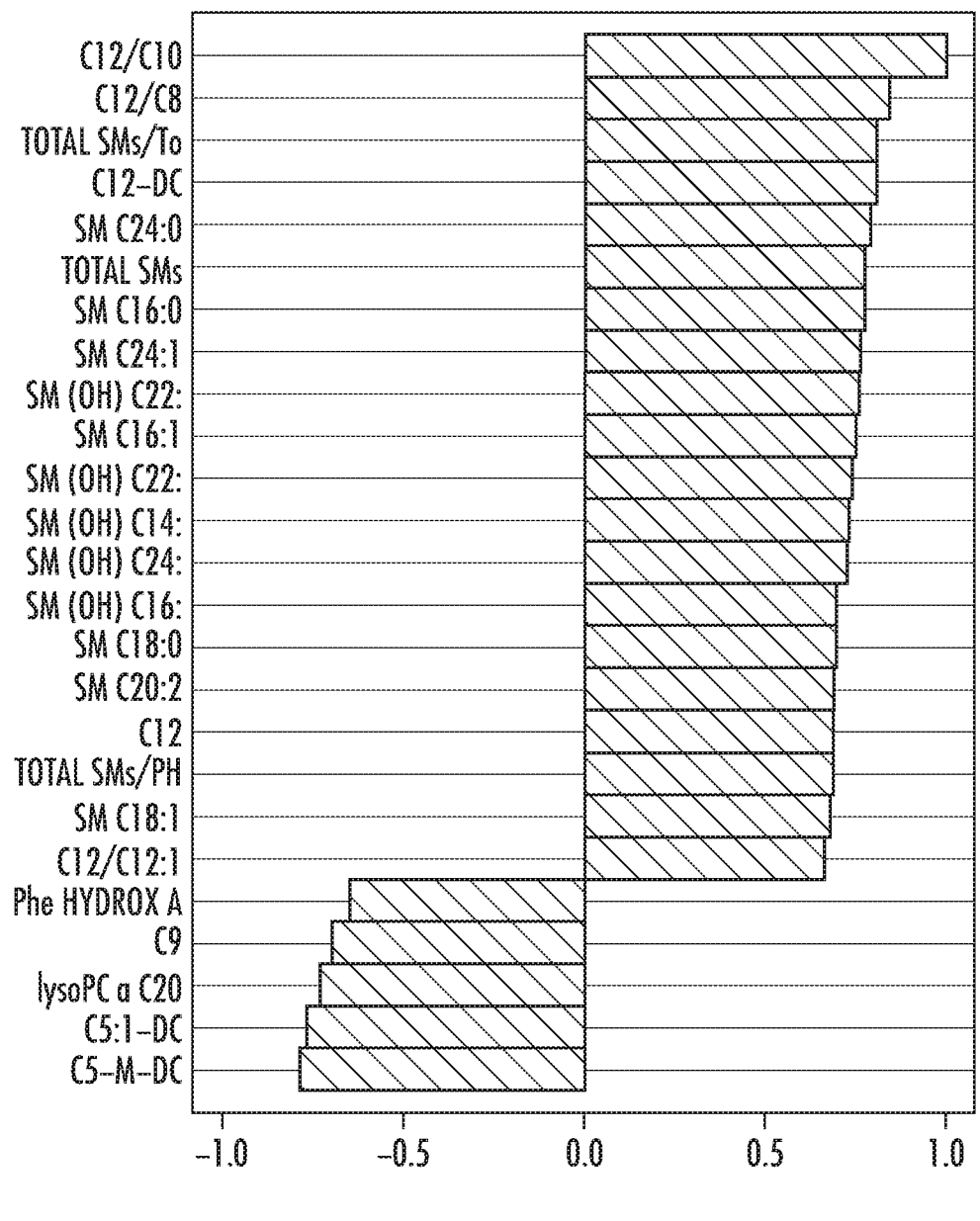
FIG. 5B: Correlation analysis of ACADM function (C12/C10) with blood metabolites in HIV and control group. Increases in ACADM function are closely followed for increases in sphingomielins and acylcarnitine C12-DC both, significantly, down regulated during HIV infection. On the other hand, HIV-elevated metabolites such C5-M-DC and Phenylalanine hydroxylase activity were, significantly, down regulated.
Figure 6A:
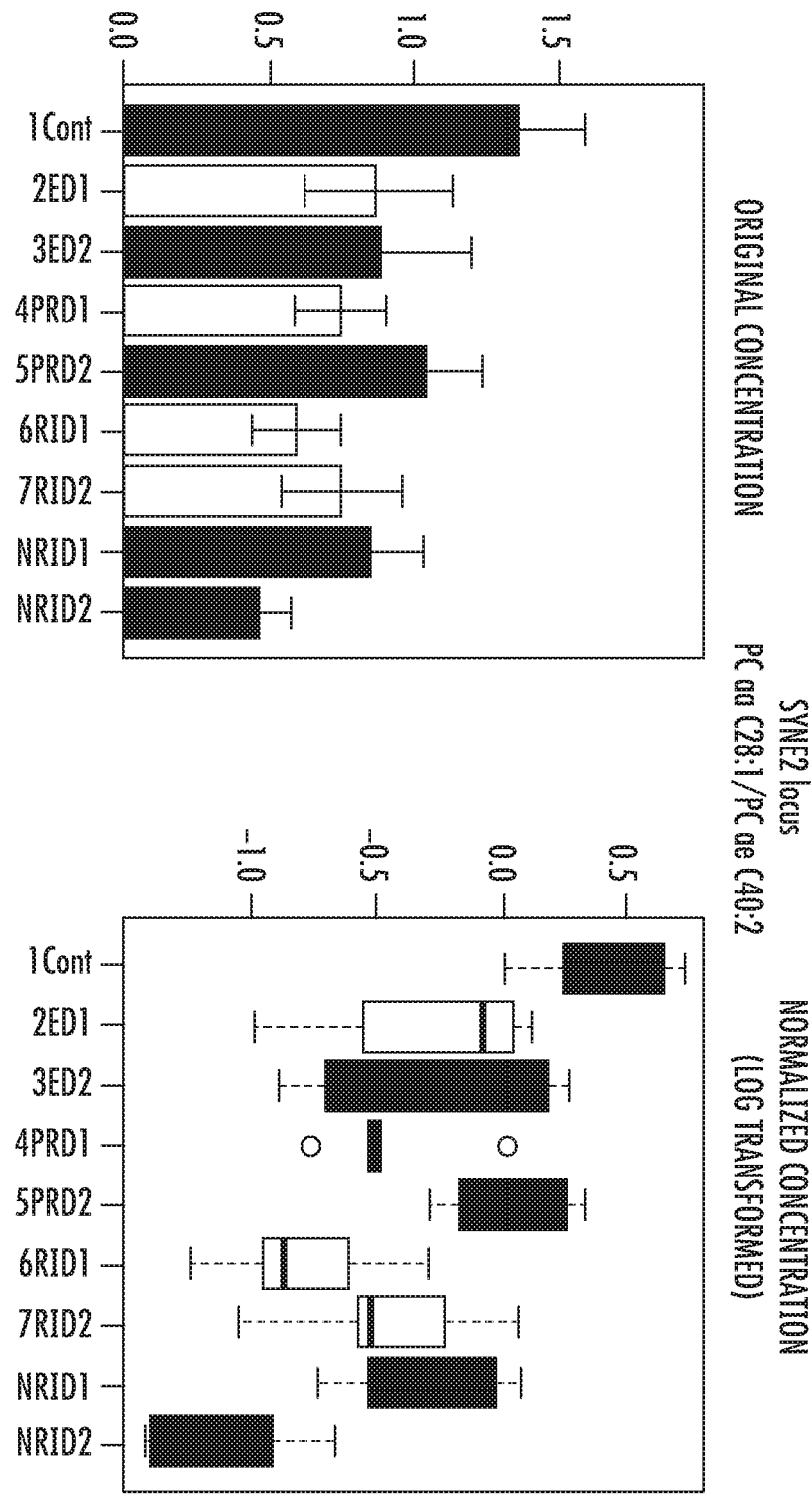
FIG. 6A: The SYNE2 locus activity is highly decreased in HIV patients compared to healthy controls particularly in the group of nonimmunologic response after 1 year of follow-up.
Figure 6B:
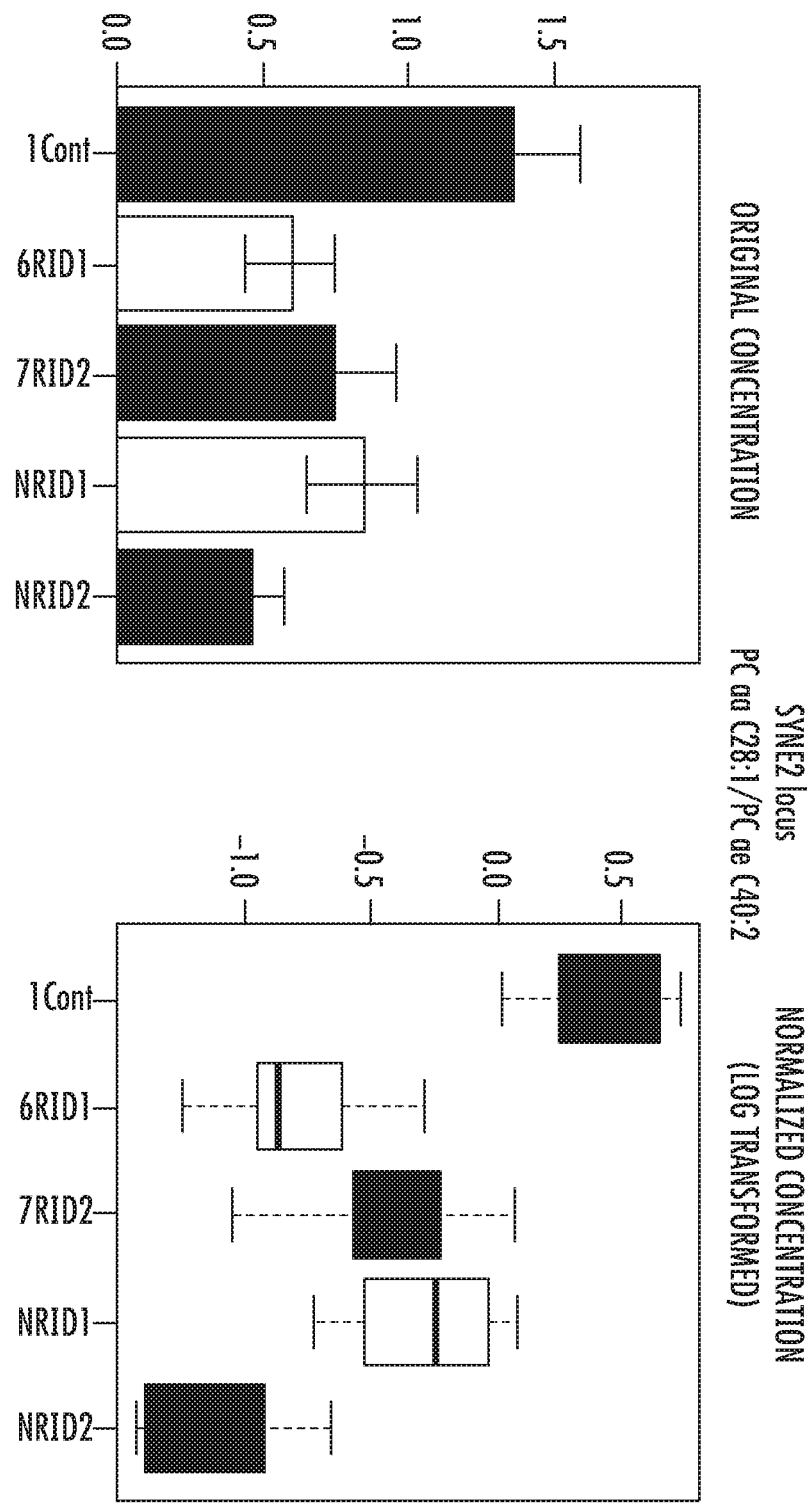
FIG. 6B: The SYNE2 locus activity is highly decreased in HIV patients particularly in the group of nonimmunologic response after 1 year of follow-up (p=1.2959E-7, −log 10(p)=6.8874, FDR=1.5798E-6) (ANOVA PostHoc) (Legend: 1Cont=Controls, 6RID1=Immunologic responders at baseline, 7RID2=Immunologic responders after 1 year, NRID1=non-Immunologic responders at baseline, NRID2=non-Immunologic responders after 1 year).
Figure 6C:
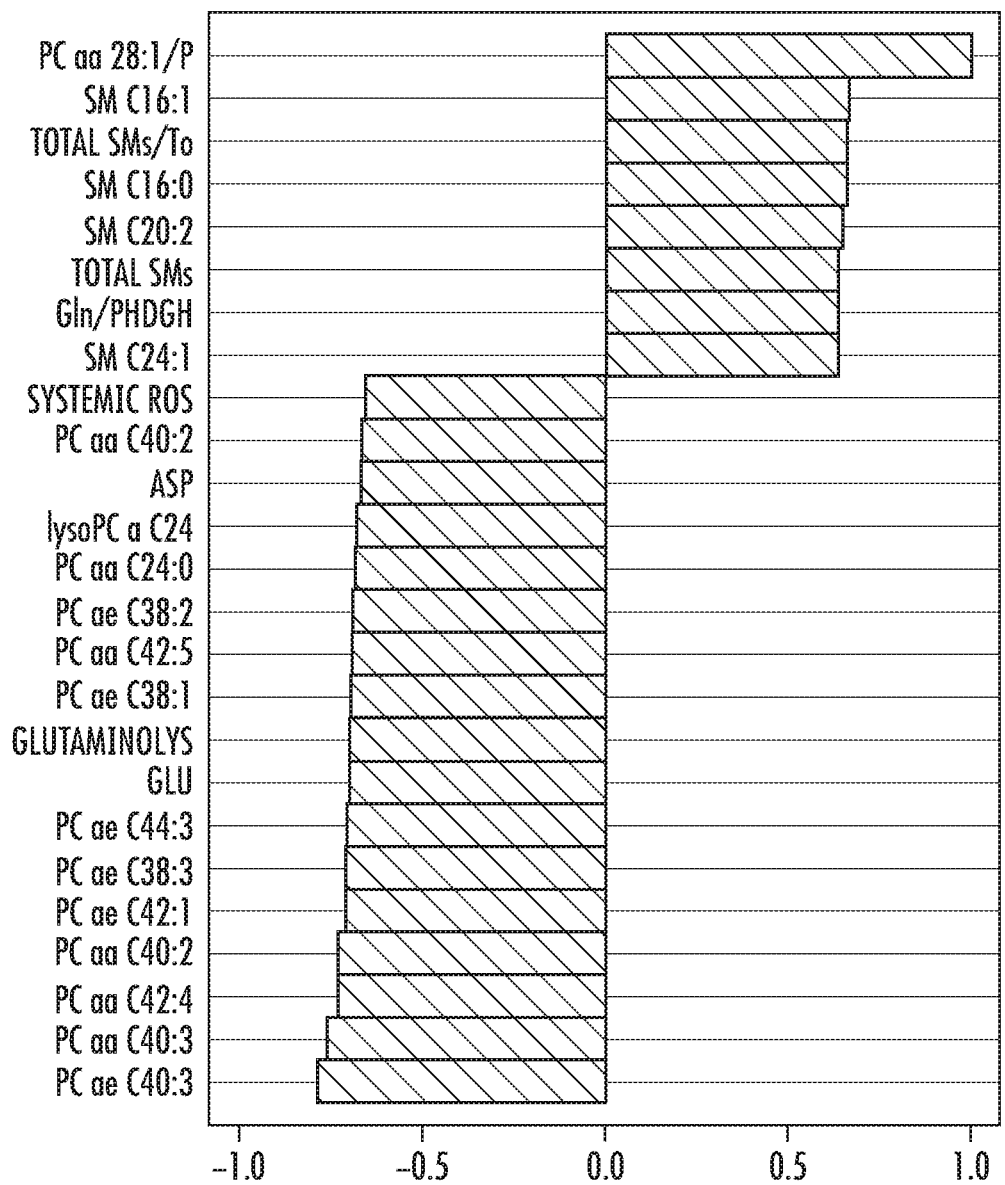
FIG. 6C: Correlation analysis of SYNE2 loccus activity (PC aa 28:1/PC ae 40:2) with blood metabolites in HIV and control group. Increases in SYNE2 function are closely followed by significant augments in Total Sphingomielins and significant drops in Systemic ROS as measured by the ratio of Sulphoxidized Methionine to Total Unmodified Methionine (Met-SO/Met).
Figure 7A:
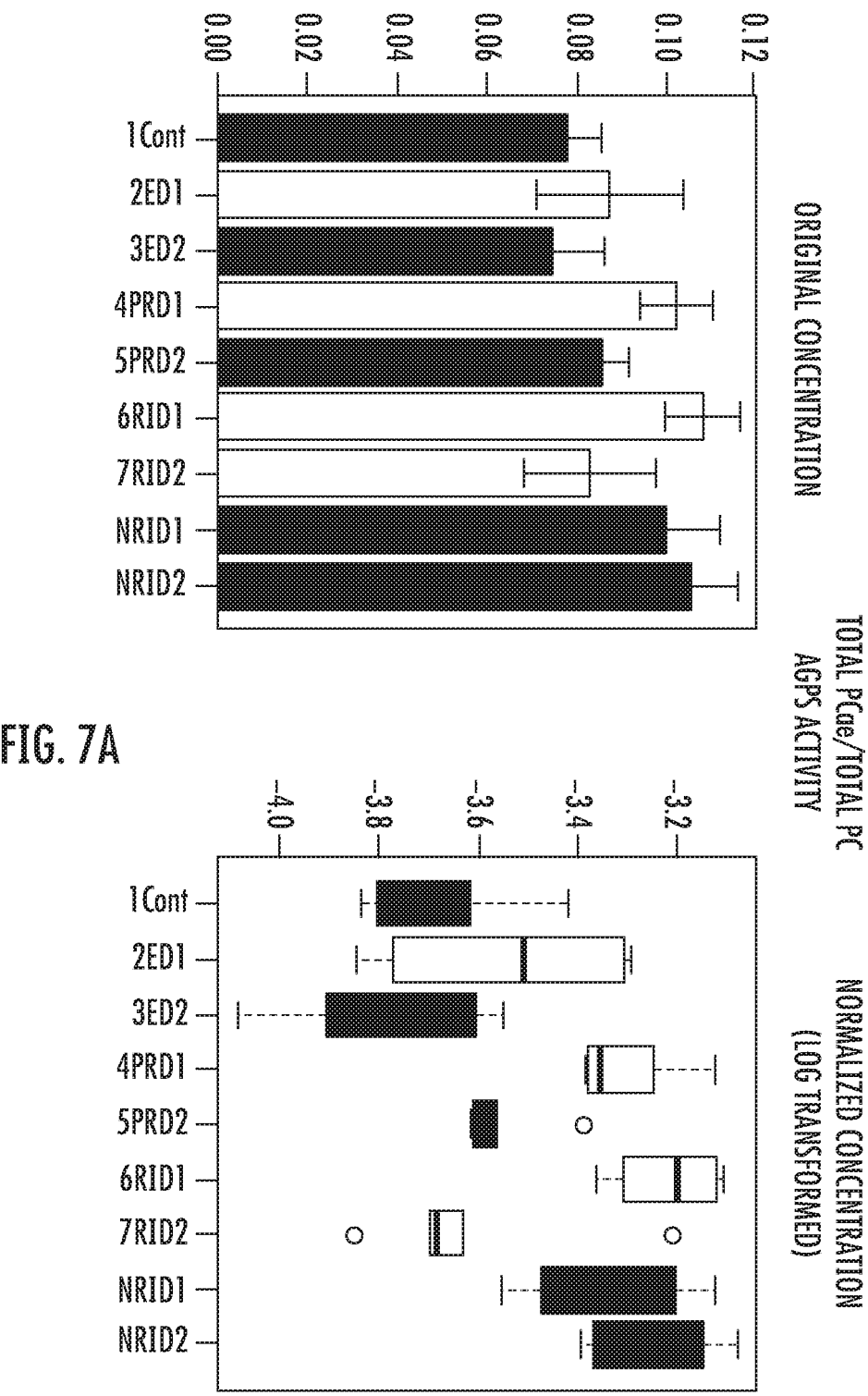
FIG. 7A: Ratio of Total PC ae to Total PC demonstrates that in all groups but not in the non-immunological responders the production of ether lipids return to normal levels one year after the first visit. The opposite is happening in the non-immunologic response group (p=1.1405E-5; −log(10(p)=4.9429; FDR=9.6586E-5) (ANOVA PostHoc) (Legend: 1Cont=Controls, 2ED1=Elite baseline; 3ED2=Elite after 1 year; 4PRD1=Rapid Progressors baseline; 5PRD2=Rapid Progressors after 1 year; 6RID1=Immunologic responders at baseline, 7RID2=Immunologic responders after 1 year, NRID1=Non-Immunologic responders at baseline, NRID2=Non-Immunologic responders after 1 year).
Figure 7C:
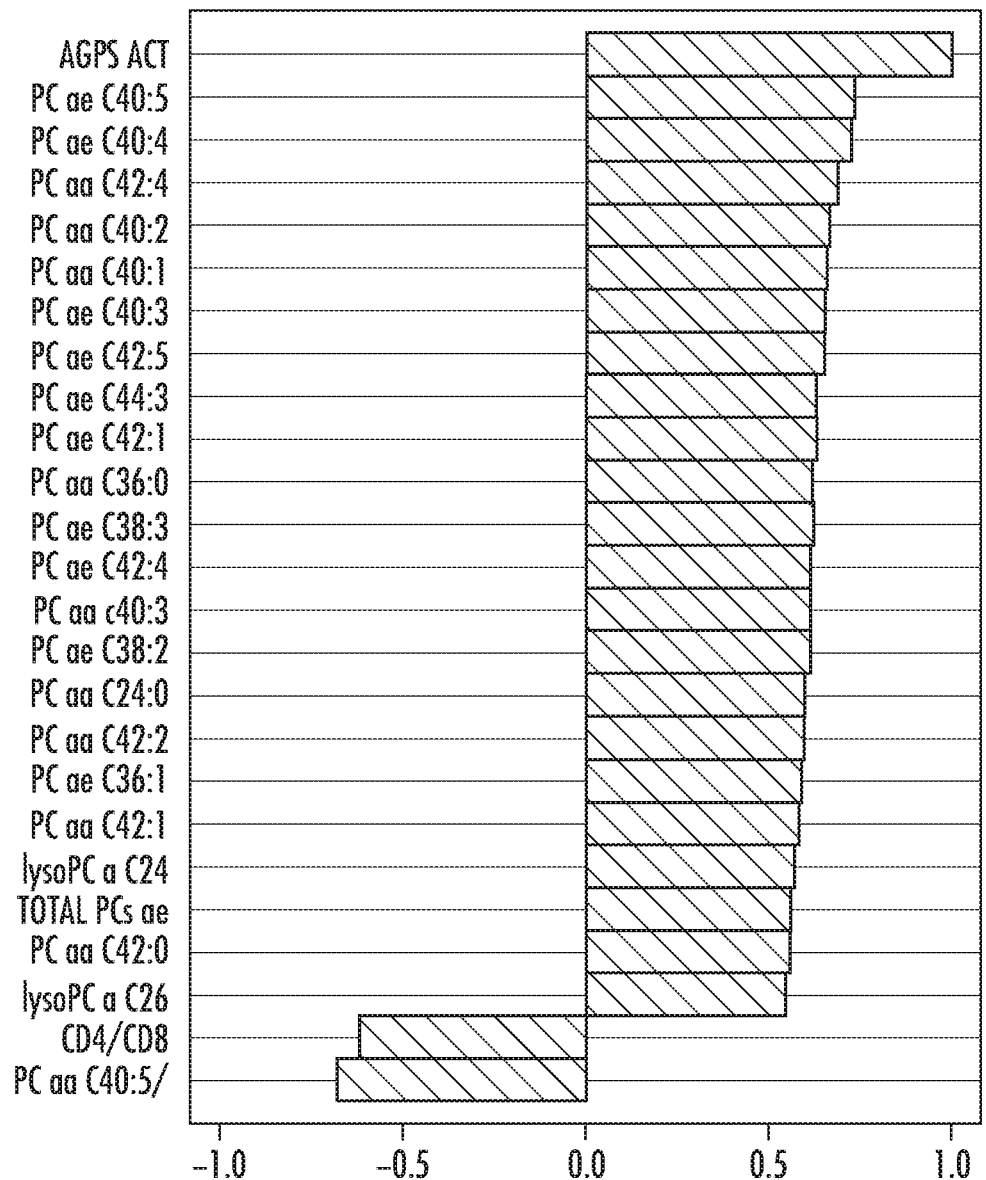
FIG. 7C: Correlation analysis of AGPS activity (Total PC ae/Total PC) with blood metabolites in HIV and control group. Increases in AGPS function are closely followed for decreases in CD4/CD8 and also in the Elongase of very-long fatty acids 2 (ELOVL2) as measured by the PC aa C40:5/PC aa 42:5 ratio.
Figure 7D:
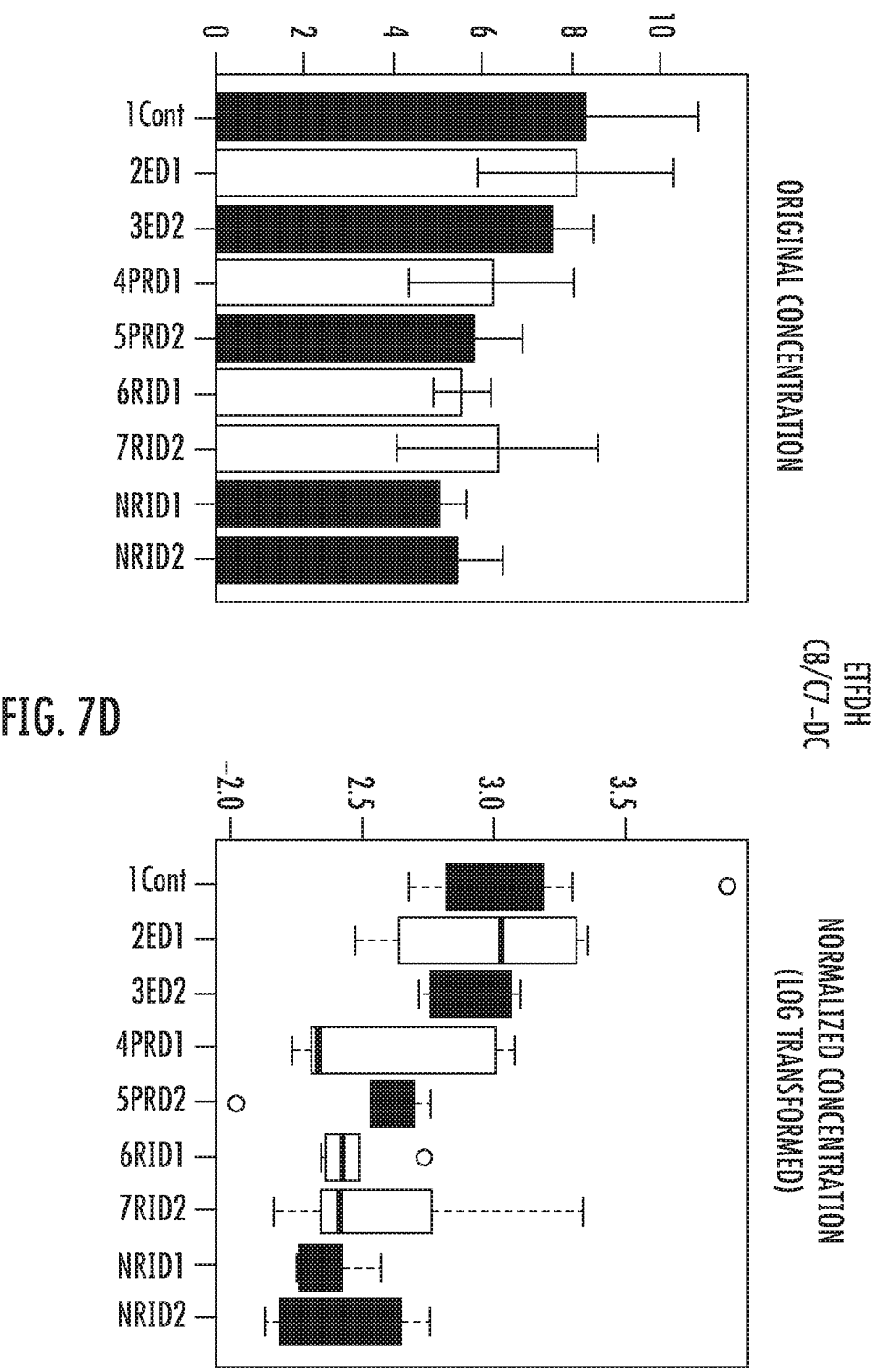
FIG. 7D: Comparison of the amount of the Electron-transferring-flavoprotein-dehydrogenase (ETFDH) present in the respective immunological groups of patients (abbreviations as above).
Figure 7E:
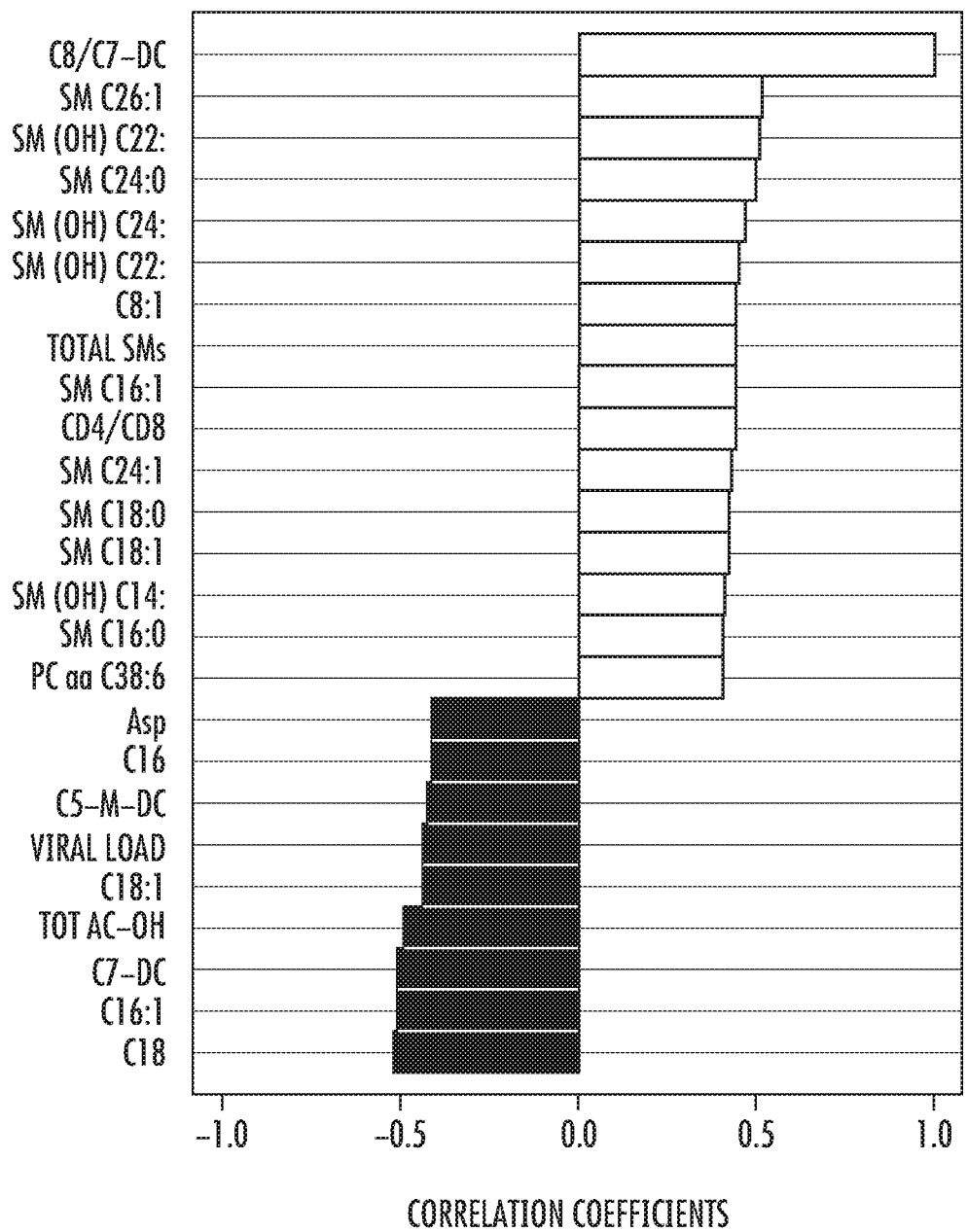
FIG. 7E: Correlation analysis of ETFDH function (C8/C7-DC) with blood metabolites in HIV and control group. Increases in ETFDH function are closely followed for increases in sphingomyelins, that were significantly down regulated during HIV infection. On the other hand, HIV-elevated metabolites such C5-M-DC and Viral Load were, significantly, down regulated.

Notably, when correlation analysis with the ratio C12/C10 is performed between HIV and controls, almost all deregulated metabolites induced by HIV infection (FIGS. 4A and B) are properly re-directed towards normality (FIG. 5B). And second, by a significant drop in de novo synthesis of sphingomyelins due to diminished SYNE2 locus, particularly in the non-immulogic response group after 1 year of follow-up, evaluated by the ratio PC as C28:1/PC ae C40:2 (p=8.4667E-7, −log 10 (p)=6.0723, FDR=1.2712E-5) (FIGS. 6A and B).

When comparing the non-immunological response group with its counterpart, a significant increase in ether lipid synthesis could be shown in the first group. It was concluded that the metabolic enzyme Alkylglyceronephosphate synthase (AGPS), a critical step in the synthesis of ether lipids, could be activated in the non-immunologic response group. In order to test this conclusion the ratio of Total PC ae to Total PC was assembled as a proxy to evaluate the AGPS activity. Results clearly confirmed the conclusion (FIG. 7) and more important, revealed that in the immunological responders the AGPS enzyme activity returned to normal levels after 1 year of follow-up. On the other hand, in the group of non-immunologic responders the enzyme activity did not return to normal levels (FIG. 7).

Further, it could surprisingly be shown in the present invention that an improvement in accuracy of screening/diagnosis of patients can be achieved by simultaneous detection of a combination of at least one acylcarnitine and at least one sphingomyelin compared with the single compounds, i.e. acylcarnitine alone or sphingomyelin alone, in a single analytical run, as demonstrated in Table 11 below.

TABLE 11

Evaluation of the performance of different combinations of acylcarnitines and sphingomyelins versus the single compounds by ROC analysis.

| Metabolite | AUC |
| --- | --- |
| C3/SM C24:0 | 0.92 |
| C0/SM C24:0 | 0.96 |
| C0/SM C20:2 | 0.95 |
| C4/SM C20:2 | 0.71 |
| C3 | 0.80 |
| C0 | 0.91 |
| C4 | 0.60 |
| SM C24:0 | 0.88 |
| SM C20:2 | 0.68 |

Plasma Metabolites Biosignature of HIV Disease Progression

Figure 8:
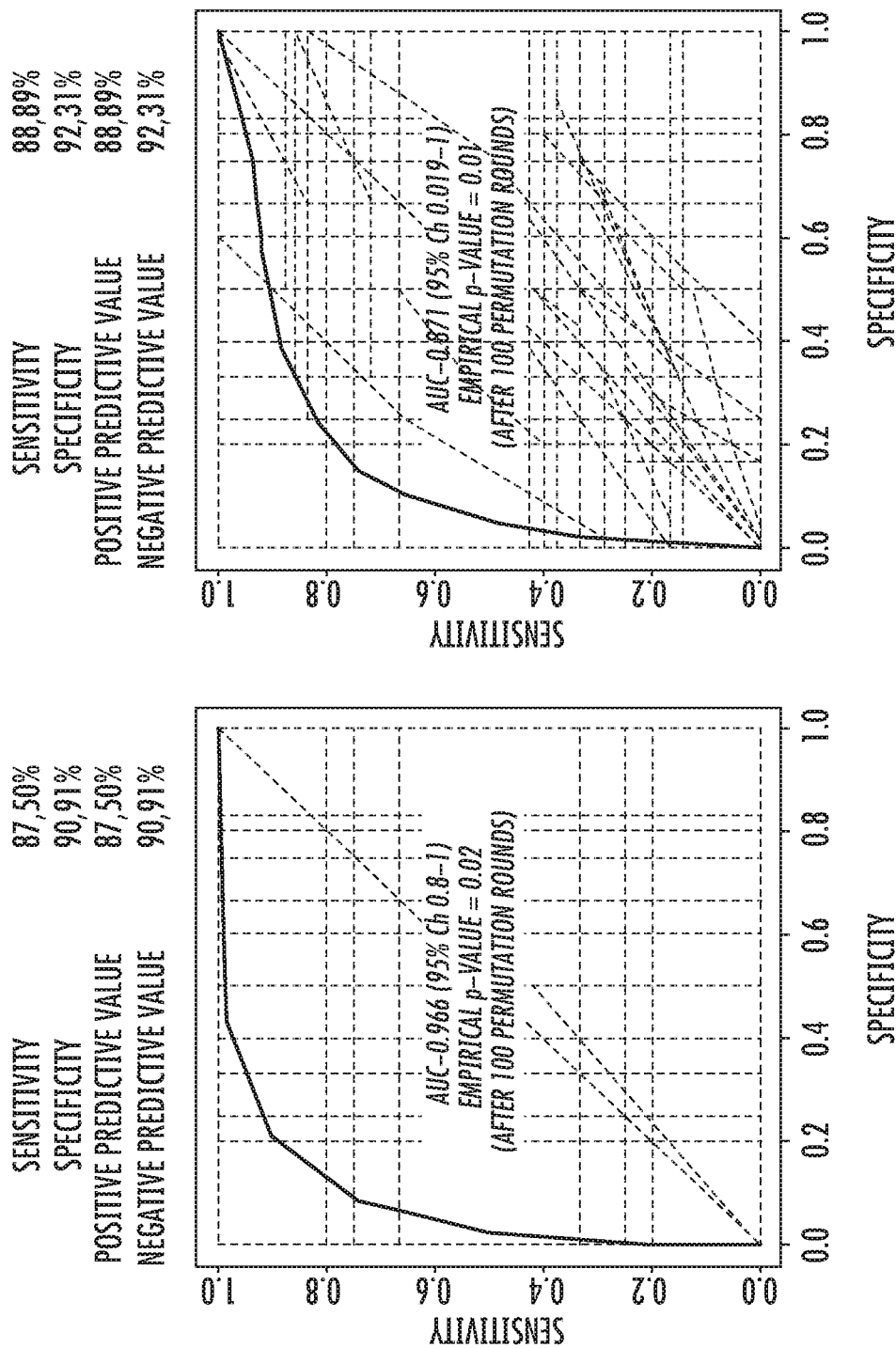
FIG. 8: HIV Good vs. Worse Prognosis: Comparison between the multivariate ROC curves obtained in training and validation sets using the 5 HIV predictive metabolites described in Table 1, pValues, after 100 permutation rounds, are also displayed.
Figure 9:
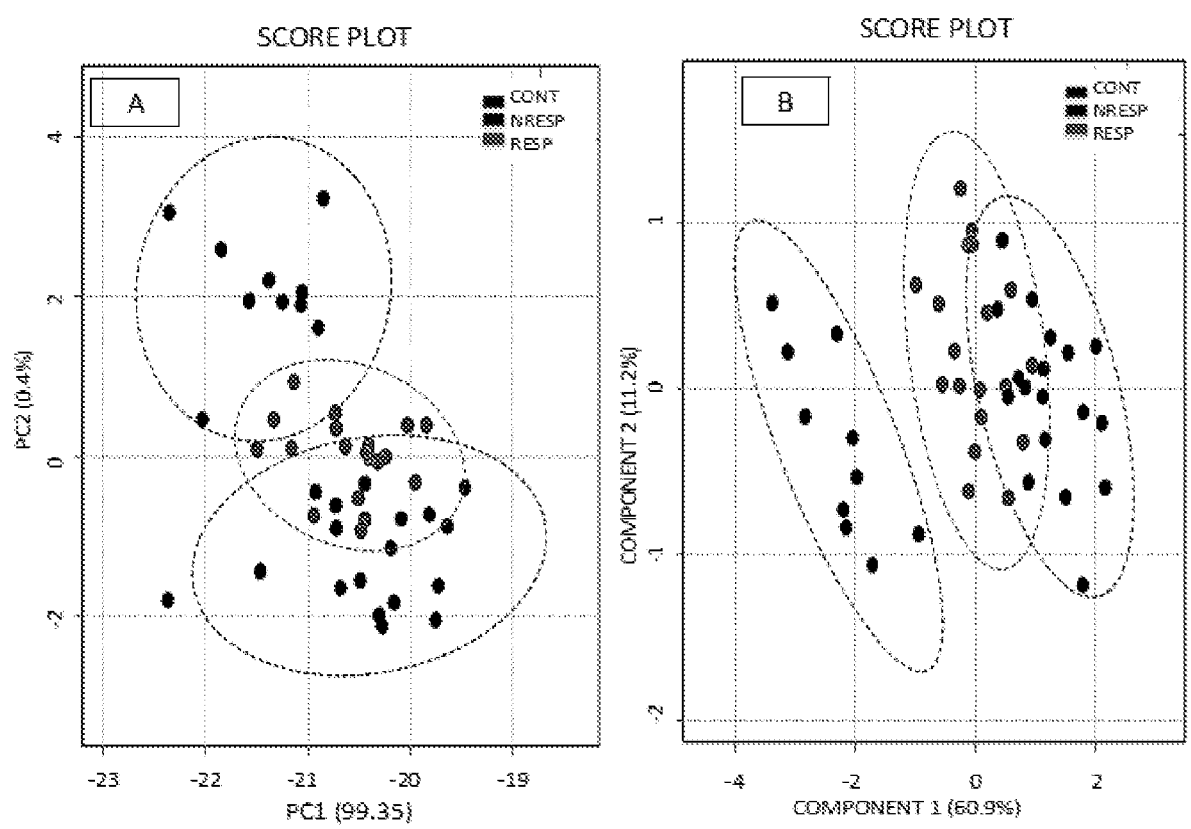
FIG. 9: PCA (A) and PLS-DA (B) two-dimensional score plots depicting differences in plasma metabolites concentrations (Cont=Healthy controls, Nresp=Worse prognosis, Resp=Good prognosis).

After Univariate and Multivariate Exploratory ROC Analysis on validation set (n=20 of which 8 were classified as good prognosis and 12 were classified as worse prognosis, 100 permutation rounds were performed), a blood metabolite signature among immunologic non-respondents and/or among rapid progressor could be identified with a sensitivity of 88.89%, a specificity of 92.31%, a positive predictive value of 88.89% and a negative predictive value of 92.31% [AUC=0.871 (95% CI; 0.619-1), empirical p-value=0.01] as shown in FIG. 8. PLS-DA and PCA analysis depicted in FIG. 9 also demonstrate differences in metabolites concentrations among controls, good prognosis and worse prognosis.

Five metabolites (Table 12) provided this plasma metabolomic biosignature of HIV disease progression: total AC-DC/C3-OH (AUC 0.84706; p-value of 8.5342E-5), Tyr/Phe/PC ae C38:4 (AUC 0.83824; p-value 4.6799E-4), Tyr/Phe/PC ae C40:6 (AUC 0.83235; p-value 4.3552E-4), C3-OH/C14:2-OH (AUC 0.82059; p-value of 4.6198E-4) and Tyr/Phe/Sum Arac PC ae (AUC 0.81765; p-value 4.558E-4).

TABLE 12

Metabolites used in multivariate analysis to predict worse prognosis for HIV patients

| Metabolites | AUC | pValue |
| --- | --- | --- |
| Total AC-DC/C3—OH | 0.84706 | 8.5342E−5 |
| Tyr/Phe/PC ae C38:4 | 0.83824 | 4.6799E−4 |
| Tyr/Phe/PC ae C40:6 | 0.83235 | 4.3552E−4 |
| C3—OH/C14:23—OH | 0.82059 | 4.6198E−4 |
| Tyr/Phe/Sum Arac PC ae | 0.81765 | 4.558E−4 |

Moreover, the performance of different combinations of at least one PC ae with at least two amino acids has been evaluated comparing non-responders versus others and compared with the performance of the single metabolites, i.e. only the PC ae or only the two amino acids. The results are shown in Table 13 below.

TABLE 13

Evaluation of the performance of different combinations of PC ae and two amino acids versus the single compounds by ROC analysis.

| Metabolite | AUC |
| --- | --- |
| PC ae C40:6/Phe/Yyr | 0.91 |
| PC ae C40:6/Tyr/Trp | 0.92 |
| PC ae C40:6/Met/Asn | 0.80 |
| PC ae C40:6/aromatic AA | 0.76 |
| Tyr | 0.73 |
| Trp | 0.54 |
| Ile | 0.52 |
| Met/Asn | 0.78 |
| Phe/Tyr | 0.79 |
| His/Ty/Phe/Trp | 0.58 |
| PC ae C40:6 | 0.74 |

It could surprisingly be shown that the combination of all three metabolites performs significantly better than the amino acid ratio of two amino acids alone or the PC ae alone.

Plasma Metabolites for Monitoring HIV Disease Activity

Figure 10A:
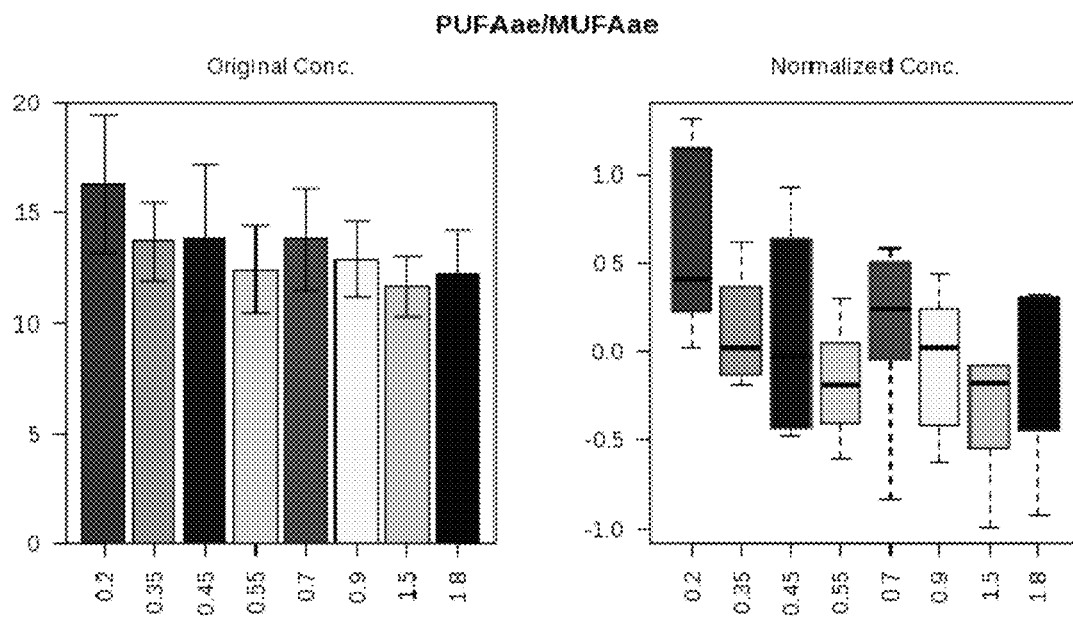
FIG. 10A: Correlation of PUFA PC ae/MUFA PC ae with ratio of CD4/DC8 cell count.
Figure 10B:
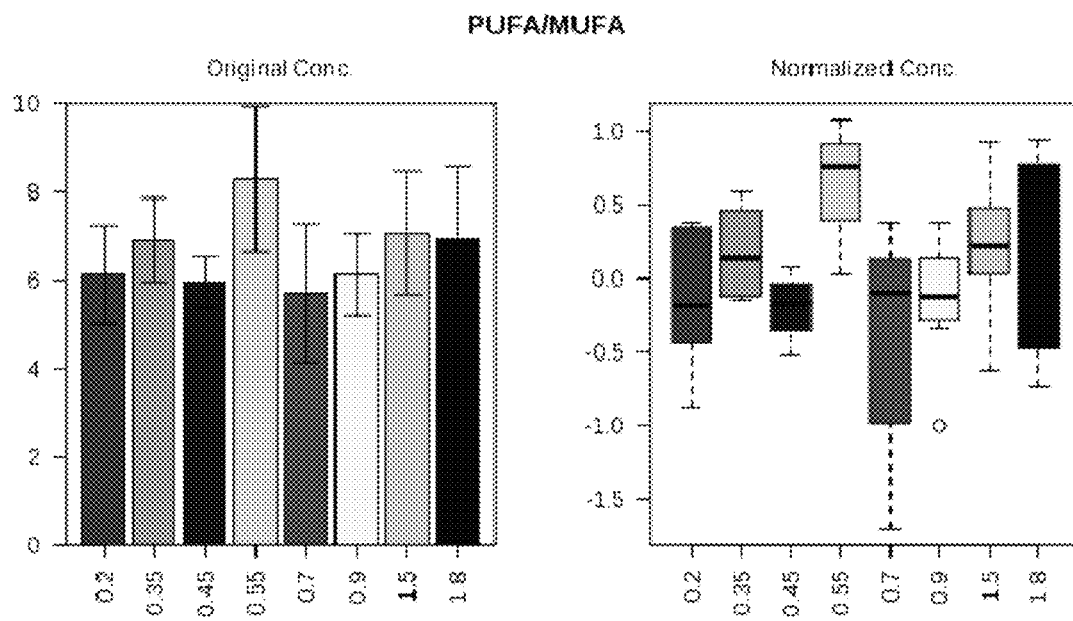
FIG. 10B: Correlation of PUFA/MUFA with ratio of CD4/DC8 cell count.
Figure 11A:
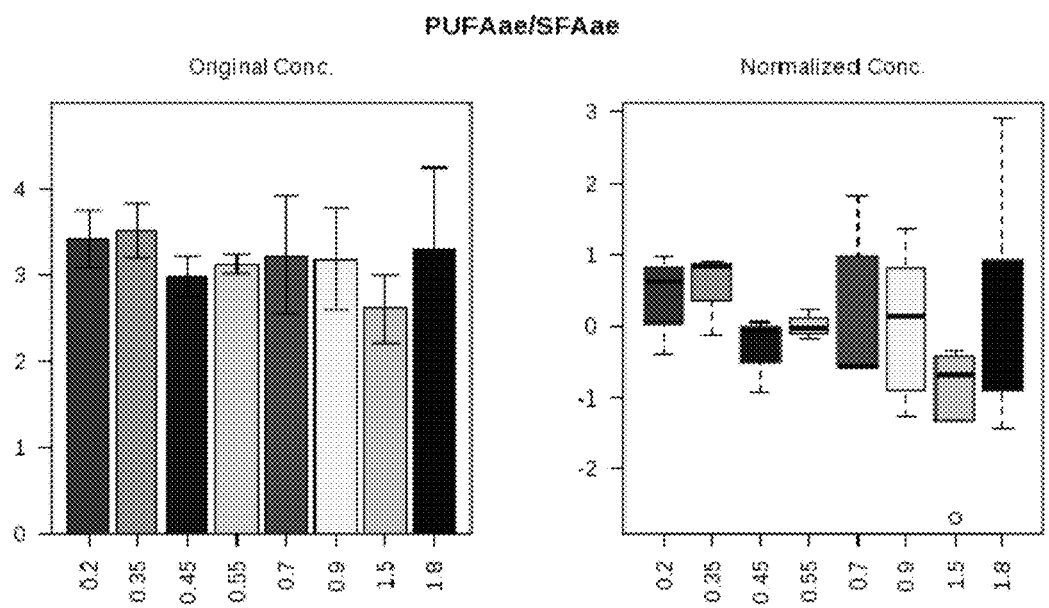
FIG. 11A: Correlation of PUFA PC ae/SFA PC ae with ratio of CD4/DC8 cell count.
Figure 11B:
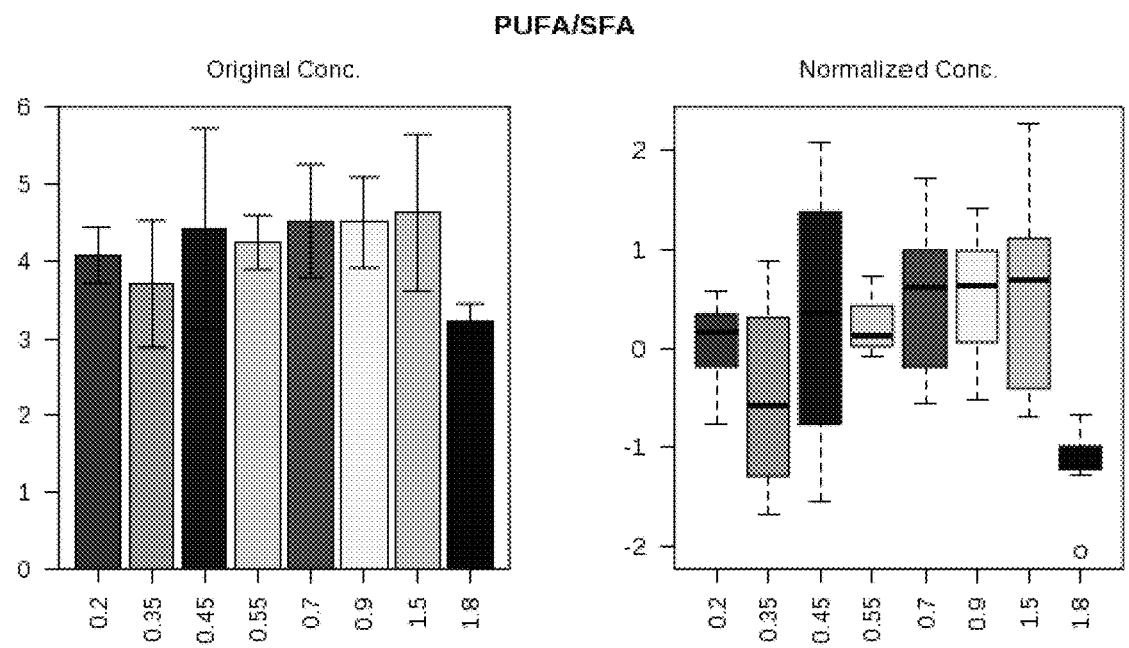
FIG. 11B: Correlation of PUFA/SFA with ratio of CD4/DC8 cell count.

As shown in FIG. 10A the combination of PUFA PC ae/MUFA PC ae shows a clear correlation with CD4/CD8 cell count as diagnostic marker for monitoring HIV activity. The selection of a subgroup of lipids (PC ae) thus clearly increases this correlation compared to a combination utilizing all lipids as shown in FIG. 10B (PUFA/MUFA). Further, the combination PUFA/SFA (FIG. 11B) does not show a correlation with CD4/CD8, whereas the selection of PC ae also improves the correlation (FIG. 11A).

Hence, it could surprisingly be shown in the present invention that a combination of metabolites comprising the ratio of total amount of arachidonic polyunsaturated etherlipids (PUPA ae) to total amount of monounsaturated fatty acid ether lipids (MUFA ae) and the ratio of total amount of monounsaturated fatty acid ether lipids (MUFA ae) to total amount of saturated fatty acids (SFA) correlates with CD4/CD8 cell count, and thus this combination of metabolites can be used as a biomarker set for monitoring of HIV disease activity in a mammalian subject.

The findings of the present invention led to the conclusion that besides HIV outcome prediction, the metabolite profile of these patients are so peculiar and specific that they permit the identification of a new diagnostic method based on blood metabolomics.

Therefore, it is possible with the biomarkers identified in the present invention in only one blood sample, to have assessment to diagnosis as well as prediction of outcome of HIV disease. The signature was validated in samples with or without detectable viral loads as well as during accute and chronic phases of the disease.

INDUSTRIAL APPLICABILITY

The present invention makes it possible to more accurately screen for and diagnose HIV in an improved manner and at an early stage of the disease. Moreover, the present invention allows for a more reliable prediction of disease progression as well as prediction of the patient's therapeutic response to antiretroviral therapy. More particularly, the methods of the invention provide new diagnostic and predictive biomarkers able to identify patients at higher risk to develop incomplete restoration of immune system after antiretroviral treatment as well as rapid progressors patients. In fact, the biomarkers according to the invention are easily detectable in biological samples, in particular in blood.

Based thereon it is possible to prepare a kit being suitable to be of assistance in more reliably screen and diagnose HIV in a patient, monitor disease progression and predict the patient's therapeutic response to antiretroviral therapy.

The invention claimed is:

1. A method for prediction of immunologic response of a mammalian subject to antiretroviral therapy, the method comprising:

measuring, utilizing a quantitative analytical method selected from chromatography, spectroscopy, and/or mass spectrometry, in a blood sample obtained from the subject the amount of at least one phosphatidylcholine with at least one acyl-alkyl group in the molecule (PC ae) and at least two amino acids;

applying descriptive analysis to data obtained from the measurements;

quantifying metabolite concentrations;

obtaining a blood plasma metabolomic biosignature of HIV disease progression; and predicting the subject's response to antiretroviral therapy as good response or worse response based upon the measurements by discriminating between elite controllers and immunologic responders and immunologic non-responders and rapid progressors, wherein a subject with good response comprise elite controllers (EC) and immunologic responder (IR), whereas subject with worse response comprise immunologic non-responders (INR) and rapid progressors (RP), elite controllers are HIV-infected patients capable of controlling virus replication at a level of <50 copies/ml for at least one year without the use of antiretroviral therapy, immunologic responders are HIV-infected patients that are characterized by undetectable viral load and high levels of CD4+T cells even after antiretroviral therapy, immunologic non-responders are patients that are characterized by an undetectable viral load but persist with low levels of CD4+T cells even after long periods of antiretroviral therapy, and rapid progressors are HIV-infected patients that develop AIDS in less than two years.

2. The method of claim 1, wherein the at least one phosphatidylcholine with at least one acyl-alkyl group in the molecule (PC ae) is selected from those included in Table 5 of the specification.

3. The method of claim 2, further comprising measuring the amount of at least one acylcarnitine.

4. The method of claim 3, wherein the at least one acylcarnitine is selected from those included in Table 2 of the specification.

5. The method of claim 1, wherein the at least two amino acids are Phe and Tyr.

* * * * *